United States Patent [19]
Fritz et al.

[11] Patent Number: 5,972,698
[45] Date of Patent: Oct. 26, 1999

[54] TRYPTASE INHIBITOR

[75] Inventors: Hans Fritz, Icking; Christian Sommerhoff, Munich, both of Germany

[73] Assignees: Novartis Corporation, Summit, N.J.; UCP Gen-Pharma AG, Zurich, Switzerland

[21] Appl. No.: 08/586,676

[22] PCT Filed: Jul. 25, 1994

[86] PCT No.: PCT/EP94/02445

§ 371 Date: Jan. 25, 1996

§ 102(e) Date: Jan. 25, 1996

[87] PCT Pub. No.: WO95/03333

PCT Pub. Date: Feb. 2, 1995

[30]   Foreign Application Priority Data

Jul. 26, 1993  [EP]  European Pat. Off. ............... 93111930

[51] Int. Cl.⁶ .................. C07K 14/815; C12N 15/11; A61K 38/58
[52] U.S. Cl. ............... 435/320.1; 435/69.2; 435/212; 514/12; 530/324; 536/23.5
[58] Field of Search .................... 435/219, 69.2, 435/172.3, 320.1, 325, 252.3, 254.11; 514/2, 826; 530/300, 324; 536/23.1, 23.5

[56]   References Cited

U.S. PATENT DOCUMENTS

| | | | |
|---|---|---|---|
| 4,595,674 | 6/1986 | Tschesche et al. | 514/9 |
| 4,666,829 | 5/1987 | Glenner et al. | 435/6 |
| 4,912,206 | 3/1990 | Goldgaber et al. | 536/23.5 |

FOREIGN PATENT DOCUMENTS

| | | |
|---|---|---|
| 0 332 576 | 2/1989 | European Pat. Off. . |
| 0 426 860 | 2/1990 | European Pat. Off. . |
| WO 90/06748 | 6/1990 | WIPO . |
| WO 90/14841 | 12/1990 | WIPO . |
| WO 91/19418 | 12/1991 | WIPO . |

*Primary Examiner*—Dian C. Jacobson
*Attorney, Agent, or Firm*—Hesna J. Pfeiffer

[57]   ABSTRACT

The present invention relates to novel inhibitors of human tryptase, to their isolation from leeches, to nucleotide sequences encoding the novel inhibtor molecules or fragments thereof, to vectors containing the coding sequence thereof, to host cells transformed with such vectors, to the recombinant production of the inibitors, to pharmaceutical compositions containing the novel inhibitor molecules, and to their use in diagnosis and therapy.

10 Claims, 21 Drawing Sheets

```
1                   5                  10                 15                 20                 25
K  K  V  C  A  C  P  K  I  L  K  P  V  C  G  S  D  G  R  T  Y  A  N  S  C
N-terminal
         Red/T                              Red/T
                                                                        Ox/T/ChT 30                 35                 40                 45
I  A  R  C  N  G  V  S  I  K  S  E  G  S  C  P  T  G  I  L  N
N-terminal        Red/T                        Red/T
Ox/T/ChT
```

FIG.8

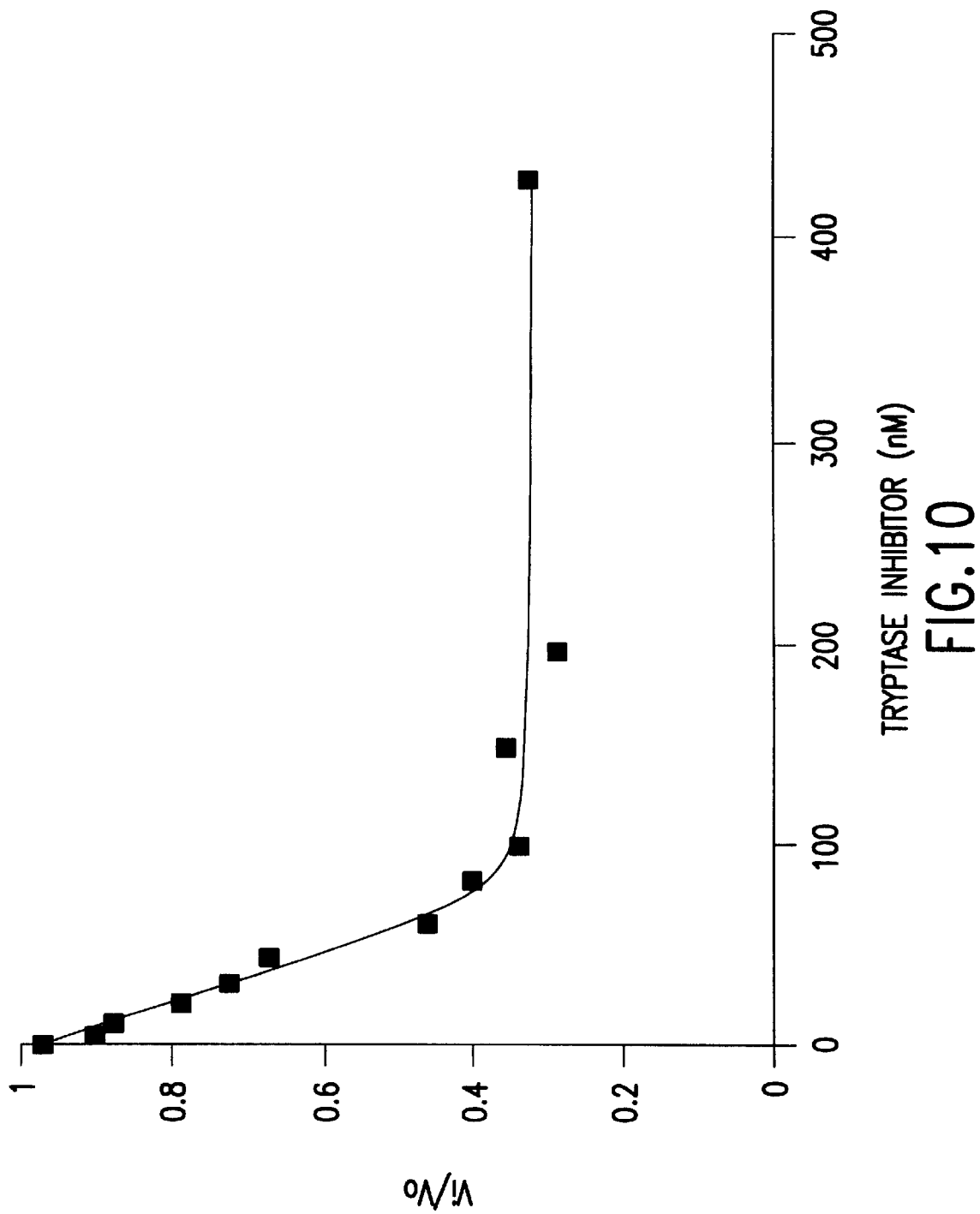

```
            LysLysValCysAlaCysProLysIleLeuLysProVal
      <---------------I------------------><--
1    AATTCGAAGAAGGTTTGCGCATGCCCAAAGATCTTGAAGCCAGTC
     GCTTCTTCCAAACGCGTACGGGTTTCTAGAACTTCGGTCAG
      <---------------II-------------><--------
```

```
     CysGlySerAspGlyArgThrTyrAlaAspSerCysIleAlaArg
     ----------------------------III-----------------
46   TGTGGTTCTGACGGTCGTACATATGCTAACTCATGCATCGCTCGT
     ACACCAAGACTGCCAGCATGTATACGATTGAGTACGTAGCGAGCA
     -----------------------IV-----------------------
```

```
     CysAsnGlyValSerIleLysSerGluGlySerCysProThrGly
     --------><----------------------V-----------------
91   TGTAACGGTGTATCGATCAAGTCTGAAGGTTCTTGTCCAACCGGT
     ACATTGCCACATAGCTAGTTCAGACTTCCAAGAACAGGTTGGCCA
     --><----------------------------VI---------
```

```
     IleLeuAsn***
     -------------->
136  ATTTTAAACTAATA 149
     TTGAATTTGATTATTCGA
     ------------------>
```

FIG.11b

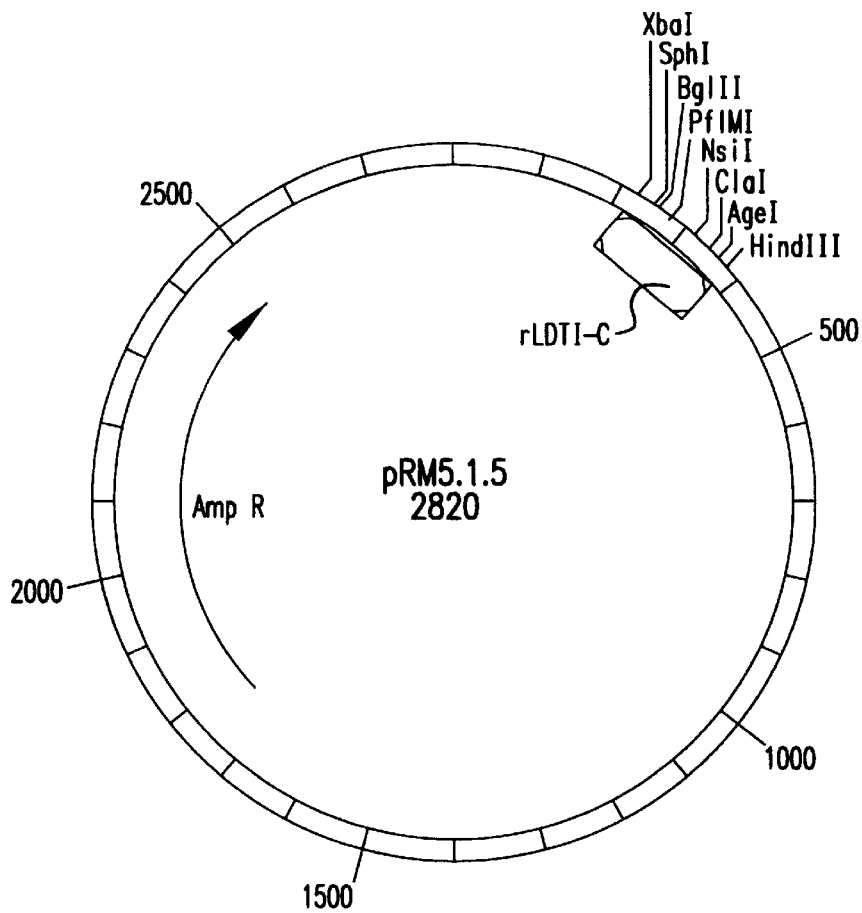

synth. Gen "rLDTI-C" (XbaI/HindIII)

```
ctagataaaagaaagaaggtttgcgcatgcccaaagatcttgaagccagtctgtggt
------+---------+---------+---------+---------+---------+
gatctattttctttcttccaaacgcgtacgggtttctagaacttcggtcagacacca
```

L D K R K K V C A C P K I L K P V C G

```
tctgacggtagaacatatgctaactcatgcatcgctagatgtaacggtgtatcgatcaag
---------+---------+---------+---------+---------+---------+
agactgccatcttgtatacgattgagtacgtagcgatctacattgccacatagctagttc
```

S D G R T Y A N S C I A R C N G V S I K

```
tctgaaggttcttgtccaaccggtatttaaactaataagct
---------+---------+---------+---------+--
agacttccaagaacaggttggccataaatttgattattcga
```

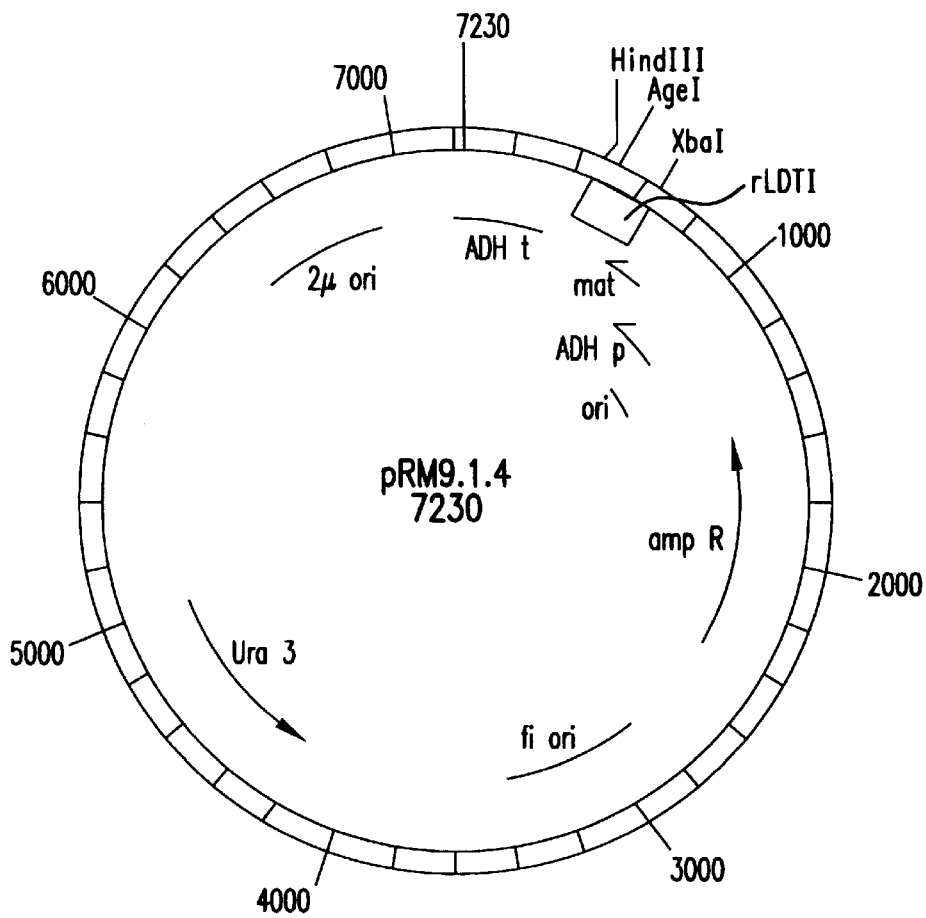

synth. Gen "rLDTI-C" (XbaI/HindIII)

```
ctagataaaagaaagaaggtttgcgcatgcccaaagatcttgaagccagtctgtggt
------+---------+---------+---------+---------+---------+
gatctattttctttcttccaaacgcgtacgggtttctagaacttcggtcagacacca

L  D  K  R  K  K  V  C  A  C  P  K  I  L  K  P  V  C  G tctgacggtagaacatatgctaactcatgcatcgctagatgtaacggtgtatcgatcaag
------+---------+---------+---------+---------+---------+
agactgccatcttgtatacgattgagtacgtagcgatctacattgccacatagctagttc

S  D  G  R  T  Y  A  N  S  C  I  A  R  C  N  G  V  S  I  K tctgaaggttcttgtccaaccggtattttaaactaataagct
------+---------+---------+---------+--
agacttccaagaacaggttggccataaaatttgattattcga

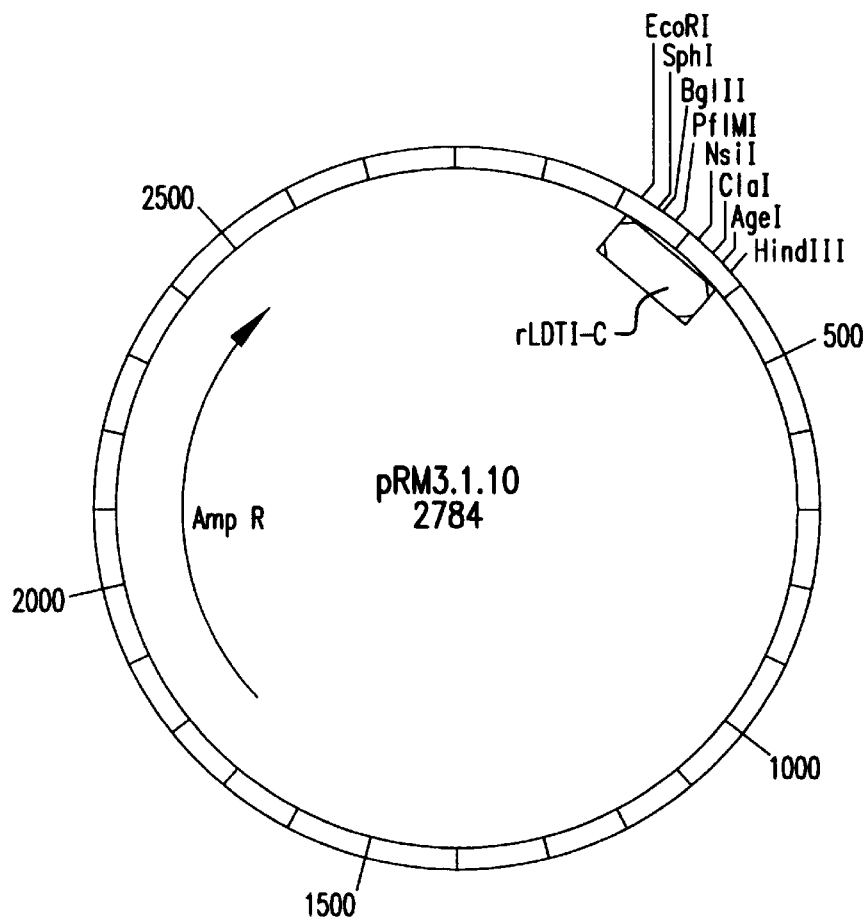

synth. Gen "rLDTI-C" (EcoRI/HindIII)

```
aattcgaagaaggtttgcgcatgcccaaagatcttgaagccagtctgtggttctgac
-----+---------+---------+---------+---------+---------+
ttaagcttcttccaaacgcgtacgggtttctagaacttcggtcagacaccaagactg
```

K  K  V  A  C  P  K  I  L  K  P  V  C  G  S  D

```
ggtcgtacatatgctaactcatgcatcgctcgttgtaacggtgtatcgatcaagtctgaa
---------+---------+---------+---------+---------+---------+
ccagcatgtatacgattgagtacgtagcgagcaacattgccacatagctagttcagactt
```

G  R  T  Y  A  N  S  C  I  A  R  C  N  G  V  S  I  K  S  E

```
ggttcttgtccaaccggtatttttaaactaataagct
---------+---------+---------+------
ccaagaacaggttggccataaaaatttgattattcga
```

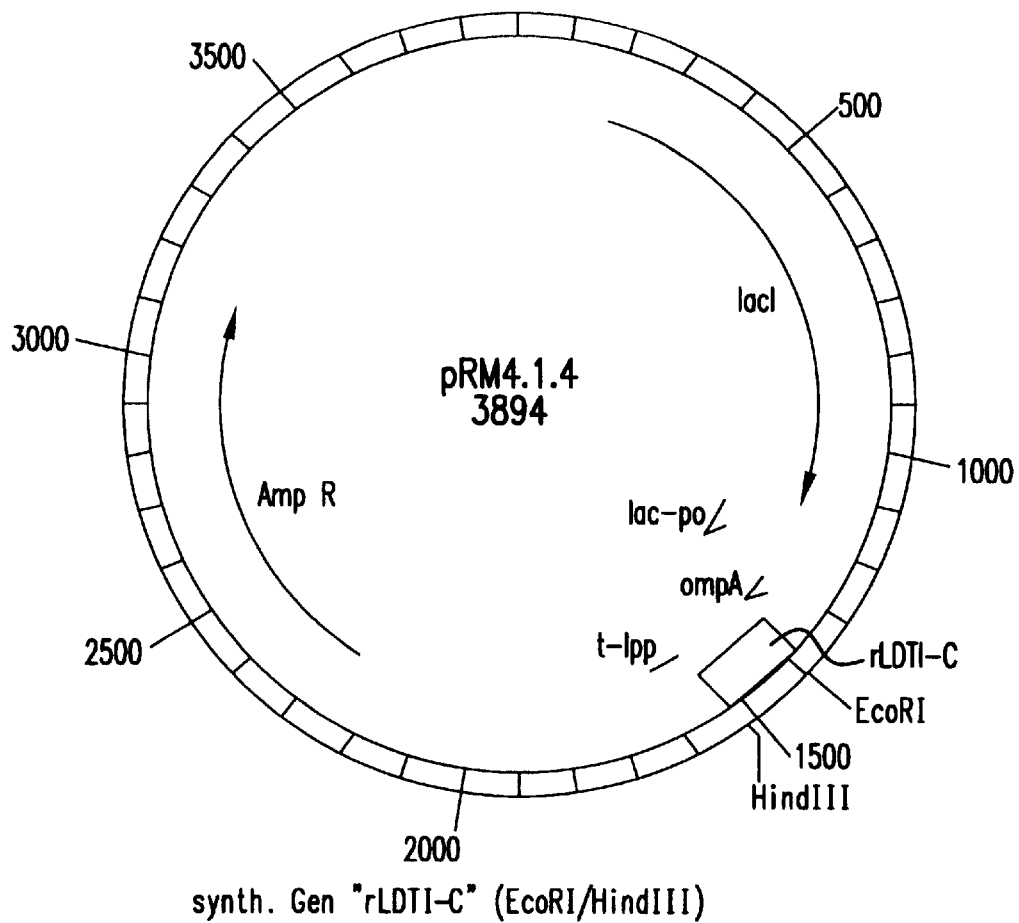

synth. Gen "rLDTI-C" (EcoRI/HindIII)

```
aattcgaagaaggtttgcgcatgcccaaagatcttgaagccagtctgtggttctgac
------+---------+---------+---------+---------+---------+
ttaagcttcttccaaacgcgtacgggtttctagaacttcggtcagacaccaagactg
```

K  K  V  A  C  P  K  I  L  K  P  V  C  G  S  D

```
ggtcgtacatatgctaactcatgcatcgctcgttgtaacggtgtatcgatcaagtctgaa
---------+---------+---------+---------+---------+---------+
ccagcatgtatacgattgagtacgtagcgagcaacattgccacatagctagttcagactt
```

G  R  T  Y  A  N  S  C  I  A  R  C  N  G  V  S  I  K  S  E

```
ggttcttgtccaaccggtatttaaactaataagct
---------+---------+---------+-----
ccaagaacaggttggccataaatttgattattcga
```

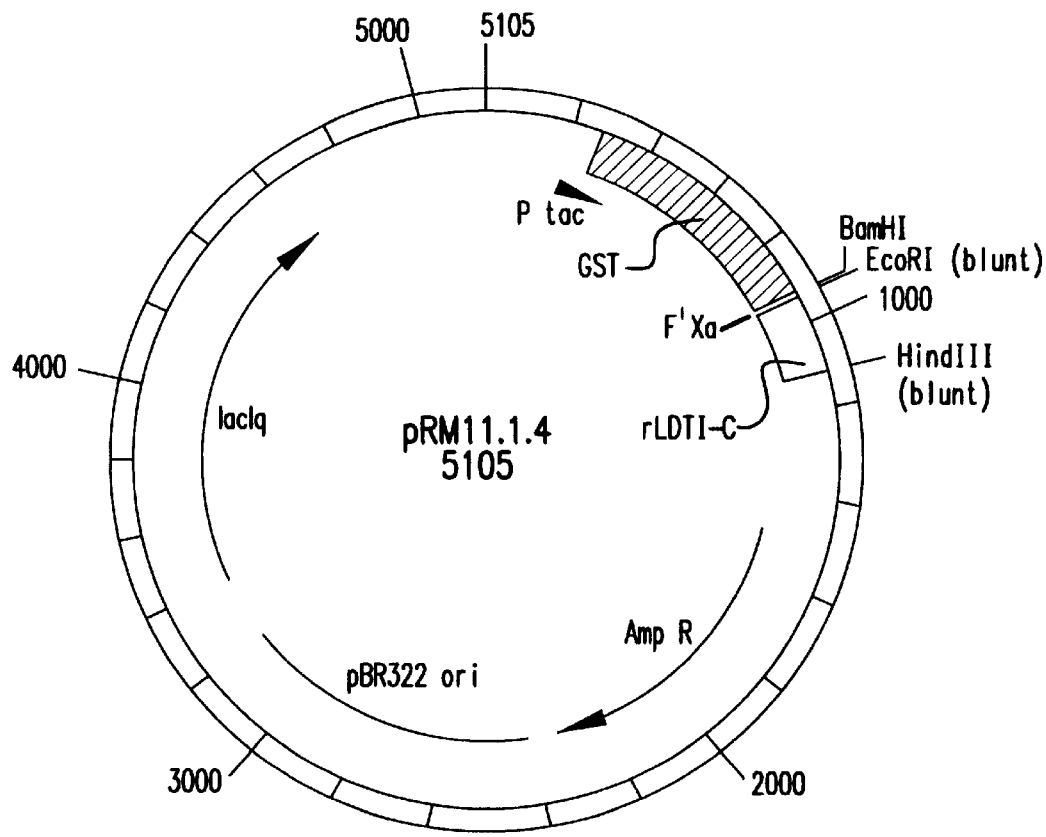

synth. Gen "rLDTI-C" (XbaI/HindIII)

```
aattcgaagaaggtttgcgcatgcccaaagatcttgaagccagtctgtggttctgac
-----+---------+---------+---------+---------+---------+
ttaagcttcttccaaacgcgtacgggtttctagaacttcggtcagacaccaagactg
```

K  K  V  A  C  P  K  I  L  K  P  V  C  G  S  D

```
ggtcgtacatatgctaactcatgcatcgctcgttgtaacggtgtatcgatcaagtctgaa
---------+---------+---------+---------+---------+---------+
ccagcatgtatacgattgagtacgtagcgagcaacattgccacatagctagttcagactt
```

G  R  T  Y  A  N  S  C  I  A  R  C  N  G  V  S  I  K  S  E

```
ggttcttgtccaaccggtatttaaactaataagct
---------+---------+---------+------
ccaagaacaggttggccataaatttgattattcga
```

TRYPTASE INHIBITOR

The present invention relates to novel inhibitors of human tryptase to their isolation from leeches, to nucleotide sequences encoding the novel inhibitor molecules or fragments thereof, to vectors containing the coding sequence thereof, to host cells transformed with such vectors, to the recombinant production of the inhibitors, to pharmaceutical compositions containing the novel inhibitor molecules, and to their use in diagnosis and therapy.

Tryptase is a tetrameric member of the family of trypsin-like serine proteinases. Tryptase is expressed virtually exclusively by mast cells [Castells Irani, 1987] and stored in large amounts in their secretory granules, constituting ~23% of the total cellular protein [Schwartz Lewis Austen, 1981]. Following activation of mast cells, tryptase is rapidly released into the extracellular space together with other preformed mediators (e.g. histamine, chymase, and proteoglycans) [Schwartz Lewis Seldin, 1981; Caughey Lazarus, 1988]. Elevated levels have been found

- in the plasma of patients with mastocytosis, after systemic anaphylaxis [Schwartz Metcalfe, 1987; Schwartz Yunginger, 1989], and during the systemic response after aspirin challenge of patients with aspirin-sensitive asthma [Bosso Schwartz, 1991],
- in bronchoalveolar lavage fluid of patients with asthma [Broide Gleich, 1991; Bousquet Chanez, 1991; Wenzel Fowler, 1988], interstitial lung diseases [Walls Bennett, 1991], and after antigen challenge of allergic patients [Castells, 1988; Butrus, 1990],
- in the skin blister fluid after cutaneous antigen challenge in patients with atopic and allergic skin disease [Shalit Schwartz, 1990; Atkins Schwartz, 1990],
- in nasal lavage fluid after local antigen challenge of patients with seasonal allergic rhinitis [Juliusson Holmberg, 1991],
- in the crevicular fluid of patients with gingivitis and periodontitis [Cox Eley, 1989, J Period Res; Eley Cox, 1992, J Dent], and
- in the lesional skin of patients with psoriasis [Harvima Naukkarinen, 1989].

In vitro studies have provided considerable evidence that tryptase is directly involved in the pathogenesis of mast cell related disorders. For example, tryptase has been suggested as a pathogenetic mediator of asthma as it increases the contractility of airway smooth muscle [Sekizawa, 1989] and inactivates vasoactive intestinal peptide, thereby destroying its potent bronchodilatatory action [Tam Caughey, 1990; Tam Franconi, 1990; Franconi, 1989]. In addition, tryptase has been shown to be a potent mitogen for fibroblasts, suggesting its involvement in the pulmonary fibrosis in asthma and interstitial lung diseases [Ruoss Hartmann, 1991; Hartmann Ruoss, 1992]. Tryptase has also been implicated in the pathogenesis of arthritis and periodontal disease, as it activates prostromelysin (=MMP-3) which in turn activates collagenase, thereby initiating the destruction of cartilage and periodontal connective tissue, respectively [Gruber Marchese, 1989; Gruber Schwartz, 1990; Cox Eley, 1989, J Period Res; Eley Cox, 1992, J Dent]. Tryptase may also promote blood clotting disorders by inactivating the procoagulant function of high molecular weight kininogen [Maier Spragg, 1983] and by cleaving fibrinogen [Schwartz Bradford Littman, 1985].

Human tryptase is virtually unique among the serine proteinases as it is fully catalytically active in plasma and in the extracellular space [Schwartz Bradford, 1986; Goldstein Leong, 1992]. Tryptase is not inhibited by the naturally occurring antiproteinases regulating the activity of other trypsin-like serine proteinases such as mucus-proteinase inhibitor (=antileukoprotease or HUSI-I), antithrombin III, alpha$_1$-proteinase inhibitor, alpha$_2$-macroglobulin, or C$_1$-esterase inhibitor [Alter Kramps, 1990; Smith Hougland, 1984; Schwartz Bradford, 1986; Harvima Schechter, 1988; Cromlish Seidah, 19873]. Furthermore, although tryptase has been known for over 10 years, inhibitors derived from non-human species or produced by peptide synthesis or recombinant technologies have not yet been described. Thus, tryptase is not affected by hirudin [Alter Kramps, 1990], aprotinin, ovomucoid inhibitor, soybean and lima bean trypsin inhibitor [Butterfield Weiler, 1990; Cromlish Seidah, 1987; Harvima Schechter, 1988], ecotin [Chung Ives, 1983], and the recombinant Kunitz-domain of the Alzheimer beta-amyloid precursor-protein [Sinha Dovey, 1990].

Although tryptase is inhibited by the general inhibitors of trypsin-like proteinases such as diisopropyl fluorophosphate, phenylmethylsulfonyl fluoride and tosyl-L-lysine chloromethyl ketone [Smith Hougland, 1984; Harvima Schechter, 1988], these compounds are unsuitable for in vivo and even for most in vitro applications due to their high toxicity and/or low stability. Furthermore, the only other inhibitors known to affect tryptase, the peptide-arginine aldehydes leupeptin and antipain [Cromlish Seidah, 1987], and certain benzamidin derivatives [Stürzebecher Prasa, 1992; Caughey, 1993] are of limited usefulness as they are relatively unspecific, and/or inhibit tryptase only with moderate affinities (K$_i$ values for the complexes in the micromolar range).

The problem of the present invention is therefore to provide a potent and efficient inhibitor of the human proteinase tryptase.

As illustrated in further detail below the present problem can be solved by providing an inhibitor polypeptide obtainable from medical leech *Hirudo medicinalis*.

BRIEF DESCRIPTION OF THE FIGURES

FIG. 8: Sequence determination of the leech-derived tryptase-inhibitor. The bars represent the overlapping fragments used in deducing the amino acid sequence. The solid bars denote the sequence obtained from the HPLC peak eluting at 25 min (see FIG. 5), and the hatched bar the additional sequence obtained from the HPLC peak eluting at 29 min. N-terminal=sequence obtained from the native inhibitor; Red/T=sequence obtained after reduction and tryptic fragmentation; Ox/T/ChT=sequence obtained after oxidation and tryptic/chymotryptic fragmentation.

FIG. 10: Effect of the leech-derived tryptase inhibitor on the tryptase-induced cleavage of vasoactive intestinal peptide (VIP). VIP was incubated with tryptase in the presence of increasing concentrations of the leech derived tryptase inhibitor. Thereafter, the amount of VIP cleaved was quantified by reversed phase HPLC. The values given are the quotient of the velocity in the presence of the inhibitor divided by the velocity in the absence of the inhibitor.

FIGS. 11A–11C: Design, DNA and amino acid sequence of synthetic rLDTI form-C gene. (a) Design of the synthetic rLDTI form-C master gene. The introduced restriction sites are shown. (b) Nucleotide and corresponding amino acid sequence of the rLDTI form-C master gene. Brackets and numbers indicate the synthetic oligonucleotides used to assemble the gene. (c) Modification of rLDTI form-C master gene by cassette mutagenesis FIGS. 12A and 12B: (a) Plasmid map of pRM 5.1.5. (b) Expression vector pRM 9.1.4. A synthetic gene for rLDTI-form C was ligated into the purified yeast secretion vector pVT102U/α, cleaved with XbaI and HindIII. Arrows indicate the direction of transcription; ADH-p, the ADH1 gene promotor; mat, the α-mating factor leader gene; ADH-t, the 3' region of the ADH1 gene including a transcription terminator signal; Ura-3, the Ura gene; amp-R, the ampicillin-resistence gene; the E.coli ori, yeast ori (2μ-ori) and the intergenic region of phage f1 (f1-ori).

FIG. 15: Plasmid map of expression vector pRM 3.1.10
FIG. 16: Plasmid map of expression vector pRM 4.1.4
FIG. 17: Plasmid map of expression vector pRM 11.1.4.

Figure 1:
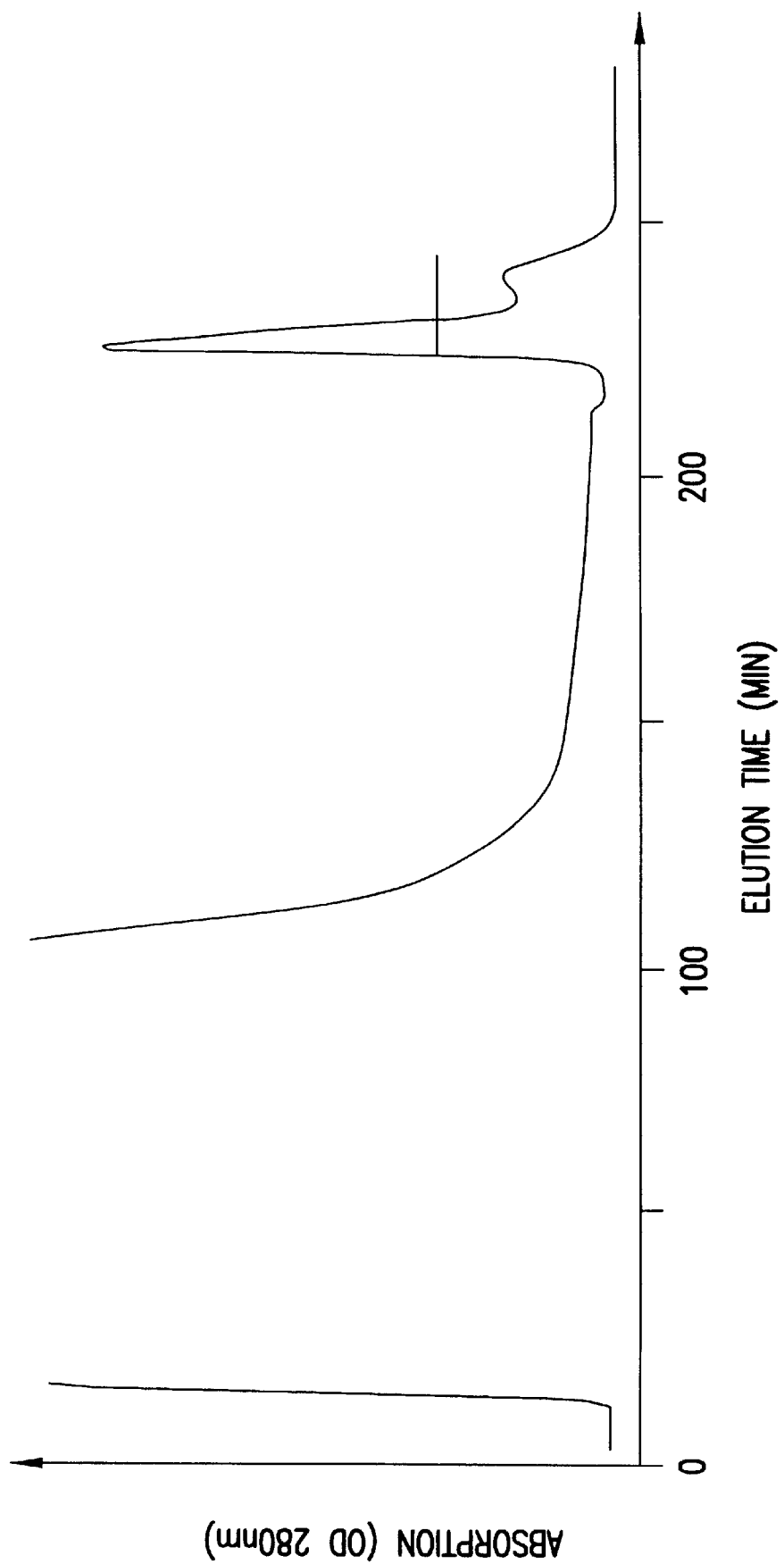
FIG. 1: Isolation of the leech-derived tryptase inhibitor by cation-exchange chromatography using SP-Sephadex. Dialysed leech extract was applied and the column was washed until the absorption of the effluent returned to baseline. Desorption was achieved with 20 mM NaP, 500 mM NaCl (pH 8.0). Fractions containing inhibitory active material (marked with a bar) were pooled.

According to a first embodiment the present invention relates to purified inhibitor molecules of human tryptase. The novel inhibitors are polypeptides obtainable from extracts of leeches, as for example the medical leech *Hirudo medicinalis*. The invention also relates to the functional equivalents of the inhibitor molecules showing tryptase inhibitor activity, and to the pharmaceutically acceptable salts of the inhibitors.

The inhibitor molecules of the present invention are characterized by their ability to inhibit human tryptase with a $K_i$ value in the range of approximately 0.1 to 10 nM, leaving the proteases involved in the human blood coagulation cascade substantially unaffected.

Preferably tryptase inhibitors are provided which are characterized by the following amino acid sequence (position 1: N-terminal amino acid Lys):

```
Lys-Lys-Val-Cys-Ala-Cys-Pro-Lys-Ile-Leu   10
Lys-Pro-Val-Cys-Gly-Ser-Asp-Gly-Arg-Thr   20
Tyr-Ala-Asn-Ser-Cys-Ile-Ala-Arg-Cys-Asn   30
Gly-Val-Ser-Ile-Lys-Ser-Glu-Gly-Ser-Cys   40
Pro-Thr-X                                 42
``` wherein X=H (SEQ ID No:1), Gly (SEQ ID NO:2) or Gly-Ile-Leu-Asn (SEQ ID NO:3).

The present invention also encompasses genetic variants, alleles or functional equivalents of the above-mentioned sequence, of which one or more of the amino acids are substituted (conservative or non-conservative) or deleted, or to which one or more amino acids are added without substantially affecting the tryptase inhibitor activity. Conservative substitutions encompass for example substitutions within the following groups of amino acids (one letter code): G,A; V,I,L; D,E; N,Q; K,R; and S,Y,N. Preferebly the amino acid addition or deletion is performed at the N- and/or C-terminal end of the above-mentioned sequence. The functional equivalents with altered and/or improved specificity and/or inhibitory efficiency can easily be prepared by a person of ordinary skill applying usual methods of peptide synthesis, or applying methods well known in the field of molecular biology, as for example site directed mutagenesis or undirected mutagenesis (e.g. using a phage display system).

Functional equivalents of the inhibitor of the present invention are for example those comprising the amino acid sequence (SEQ ID NO:21)

```
                R¹-Cys-Pro-Lys-Ile-Leu
    Lys-Pro-Val-Z-Gly-Ser-Asp-Gly-Arg-Thr
         Tyr-Ala-Asn-Ser-Cys-Ile-Ala-R²
``` wherein
the N-terminal residue R¹ represents Ala- or Cys-Ala-;
the C-terminal residue R² represents -Arg or -Arg-Cys; and
Z defines any, preferably any naturally occurring, amino acid.

Moreover, based on the teaching of the present invention a person of ordinary skill will be enabled to prepare fragments of the natural forms of the inhibitor still showing the desired tryptase inhibiting activity.

The naturally occurring forms of the claimed inhibitor molecules may either be isolated from leech, preferably the medical leech *Hirudo medicinalis*, or may be prepared by peptide synthesis or recombinant DNA technology.

According to a further aspect of the present invention a synthetic gene coding for form C (SEQ ID NO:3) of the leech derived tryptase inhibitor (LDTI-C) was designed, cloned and expressed in *Escherichia coli* and *Saccharomyces cerevisiae*. The coding fragment was assembled via 6 oligonucleotides, it contains linker sequences, stop codons and selected recognition sites for further modifications, for example by cassette mutagenesis. Strong expression of the recombinant form C inhibitor (rLDTI-C) was found using *Saccharomyces cerevisiae* secretion vector pVT102U/alpha and strain S-78. The secreted material was isolated by centrifugation and cross-flow filtration, and further purified by cation exchange chromatography, it is inhibitorily active and about 85% pure. Amino acid sequencing showed that rLDTI-C is predominantly correct processed at the junction between the alpha mating factor leader peptide and the first amino acids of LDTI-C; only minor amounts of truncated forms were detected. The far UV-CD spectrum of the recombinant molecule is typical for a folded protein containing secondary structural elements. The molecular mass of HPLC purified material is 4738±4 Da as determined by electrospray ionization mass spectrometry. The rLDTI-C displays equilibrium dissociation constants with bovine trypsin and human tryptase which are nearly identical to those of the natural one. The expected expression products encoded within the expression vector were also identified in vitro, using a S30 transcription translation system.

The proteins presented in this invention are the first compounds known to be efficient inhibitors of tryptase. Thus, the leech-derived tryptase inhibitors reduce the catalytic activity of tryptase, the $K_i$ value of the enzyme-inhibitor complex being in the nanomolar range. Moreover, the inhibitors affect not only the tryptase-induced cleavage of the peptide-nitroanilid substrate used as a tool to determine the activity of the proteinase in vitro. They also affect the cleavage of vasoactive intestinal peptide (VIP) and of kininogen, representatives of the peptides and proteins thought to be biologically relevant substrates of tryptase. In addition, the inhibitors efficiently diminish the tryptase-induced growth of human keratinocytes—an example of the direct cellular effects of tryptase—without causing apparent cytotoxic or other side effects.

Besides having a high affinity for tryptase, the leech-derived tryptase inhibitors are highly specific. Thus, with the exception of the pancreatic proteinases trypsin and chymotrypsin, other serine proteinases are not or only marginally inhibited, the $K_i$ values for the enzyme-inhibitor complexes being at least 200 times higher than for the complex with tryptase. Their specificity is illustrated by the lacking effect on the blood coagulation ex vivo, verifying that the proteinases involved in the coagulation cascade are not affected.

Thus, the leech-derived tryptase inhibitors of the present invention will allow for the first time the inhibition of tryptase with high affinity and specificity. Consequently, the inhibitors provide the prospect to effectively block pathophysiologic events involving the cleavage of proteins and peptides and/or the activation of cells by tryptase.

Therefore, it is an object of the current invention to apply the inhibitors as probes in the diagnosis well as drugs in the therapy of tryptase- and mast cell related diseases.

According to a further preferred embodiment of the present invention nucleotide sequences, as for example DNA and RNA sequences, are provided which encode a polypeptide with tryptase inhibitor activity or fragments thereof. Preferably polynucleotide molecules comprising the following general nucleotide sequence (SEQ ID NO:4) are provided:

```
5'
  1 AARAARGTNTGYGCNTGYCCNAARATHYTNAARCCNGTNTGYGGNWSNGA
 51 YGGNMGNACNTAYGCNAAYWSNTGYATHGCNMGNTGYAAYGGNGTNWSNA
101 THAARWSNGARGGNWSNTGYCCNACNX
                            3'
``` wherein R denotes A or G; M denotes A or C; W denotes A or T; S denotes C or G; Y denotes C or T; H denotes A, C, or T; N denotes any nucleotide; and X denotes —OH (SEQ ID NO:4), GGN (SEQ ID NO:5) or GGN ATH YTN AAY (SEQ ID NO:6). The invention also relates to the complementary strand thereof; and the DNA sequences which hybridize, preferably under stringent conditions, to the afore-mentioned DNA sequence.

Preferably the polynucleotides of the present invention comprise a nucleotide sequence substantially corresponding to nucleotide residues 1 to 149, or more preferably 7 to 144 of SEQ ID NO:7; or fragments thereof comprising at least 15 to 21 consecutive nucleotides of SEQ ID NO:7. Within the scope of the invention are also complementary polynucleotides comprising a nucleotide sequence substantially corresponding to nucleotide residues 1 to 149, or preferably 10 to 147 of SEQ ID NO:8; or fragments thereof comprising at least 15 to 21 consecutive nucleotides of SEQ ID NO:8. Preferably, these fragments are tryptase inhibitor specific or functional derivatives of these nucleotide sequences.

According to a further embodiment the present invention refers to an oligonucleotide which hybridizes, preferably under stringent conditions, to a nucleotide sequence encoding a polypeptide with tryptase inhibitor activity. Preferably, this oligonucleotide comprises a nucleotide sequence which is substantially complementary to the nucleotide sequence from residue 22 to residue 87 of SEQ ID NO:7.

Another embodiment of the invention refers to polynucleotides encoding a polypeptide with tryptase inhibitor activity which polynucleotides being obtainable by hybridizing, preferably under stringent conditions, with an oligonucleotide as specified above; as well as to polypeptides encoded by said polynucleotides. Suitable stringent conditions can be determined easily by one skilled in the art.

Also within the scope of the present invention are the polynucleotide sequence of SEQ ID NO:9, and functional equivalents thereof.

The present invention also encompasses vector molecules for the transformation of eucaryotic or procaryotic hosts, comprising a DNA molecule as defined above. For example, the vector may be a virus or a plasmid containing the inhibitor encoding DNA sequence in functional relation with suitable transcriptional and translational regulatory sequences well known in the art. The coding sequence may also be linked to suitable autonomously replicating sequences (ARS). Suitable host cells may be transformed with a vector containing the tryptase inhibitor coding sequence, and the inhibitor produced by the host cells may be expressed and isolated in a suitable way from the the cell culture.

A further embodiment of the invention is a polypeptide expression cassette comprising a promoter operably linked to a DNA sequence coding for the polypeptide and to a DNA sequence containing transcription termination signals. In hosts capable of secreting expressed polypeptides, the expression cassette preferably comprises a promoter operably linked to a first DNA sequence encoding a signal peptide linked in the proper reading frame to a second DNA sequence coding for the inventive polypeptide, and a DNA sequence containing transcription termination signals.

In a preferred embodiment, the promoter, the signal sequence and the terminator are recognized by the yeast expression system.

Promoters suitable for expression in a certain host are well known. Examples are the promoter of the TRP1 gene, the ADHI or ADHII gene, acid phosphatase (PHO5) gene, CUP1 gene, iso-cytochrome c gene, or a promoter of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes, or a promoter of the yeast mating pheromone genes coding for the a- or α-factor, can be used. Preferred vectors of the present invention contain, e.g., promoters with transcriptional control that can be turned on or off by variation of the growth conditions, e.g. the promoter of the PHO5 or the CUP1 gene. For example, the PHO5 promoter can be repressed or derepressed at will, solely by increasing or decreasing the concentration of inorganic phosphate in the medium and the CUP1 promoter can be turned on by the addition of $Cu^{2+}$-ions to the medium, e.g., in the form of a copper salt. Especially preferred are the GAPDH and the yeast CUP1 promoter.

The DNA sequence encoding a signal peptide ("signal sequence"), e.g. a yeast signal peptide, is preferably derived from a gene, e.g. a yeast gene, coding for a polypeptide which is ordinarily secreted. Yeast signal sequences are, for example, the signal and prepro sequences of the yeast invertase (SUC2), α-factor, pheromone peptidase (KEX1), "killer toxin" and repressible acid phosphatase (PHO5) genes and the glucoamylase signal sequence from Aspergillus awamori. Additional sequences, such as pro- or spacer-sequences which may carry specific processing signals can also be included in the constructions to facilitate accurate processing of precursor molecules. For example, the processing signals contain a Lys-Arg residue, which is recognized by a yeast endopeptidase located in the Golgi membranes. The preferred signal sequences according to the present invention are those of the yeast PHO5 gene, the α-factor and of the yeast invertase gene (SUC2).

A DNA sequence containing transcription termination signals, e.g. yeast transcription termination signals, is preferably the 3' flanking sequence of a gene, e.g. a yeast gene, which contains proper signals for transcription termination and polyadenylation. The preferred flanking sequence is that of the yeast PHO5 and the α-factor gene.

The DNA coding for the polypeptide according to the invention may be isolated from a gene bank of the natural host (the medical leech *Hirudo medicinalis*) by methods known in the art or synthesized by PCR using, e.g., the preferred codon usage of the host.

The promoter, the DNA sequence coding for the signal peptide, the DNA sequence coding for the polypeptide and the DNA sequence containing transcription termination signals are operably linked to each other, i.e. they are juxtaposed in such a manner that their normal functions are maintained. The array is such that the promoter effects proper expression of the signal sequence-polypeptide gene complex, the transcription termination signals effect proper termination of transcription and polyadenylation. The signal sequence is linked in the proper reading frame to the polypeptide gene in such a manner that the last codon of the signal sequence is directly linked to the first codon of the gene for the polypeptide. The yeast promoter is preferably joined to the signal sequence between the major mRNA start and the ATG naturally linked to the promoter gene. The signal sequence has its own ATG for translation initiation. The junction of these sequences may, for example, be effected by means of synthetic oligo-deoxynucleotide linkers carrying the recognition sequence of an endonuclease. Examples for related expression cassettes are described e.g. in EP-A-341215.

Preferred expression cassettes comprise the CUP1 or the GAPDH promoter, the α-factor or the yeast invertase leader sequence, the tryptase inhibitor gene and the α-factor terminator.

Especially preferred expression cassette comprise a recombinant DNA molecule as described in Example 9 or a functional fragment or derivative thereof.

A further embodiment of the invention concerns a recombinant plasmid comprising a polypeptide expression cassette as described above.

Apart from the polypeptide expression cassette the expression plasmids according to the invention can comprise a DNA segment originating from two-micron DNA containing the origin of replication or, if a two-micron DNA free strain of yeast is used, total two-micron DNA. The latter type of plasmids is preferred. For example, the plasmids according to the invention may contain the complete two-micron DNA in an uninterrupted form, i.e. two-micron DNA is cleaved once with a restriction endonuclease, the linearized DNA is linked with the other components of the vector prior to recircularization. The restriction site is chosen such that normal function of the REP1, REP2 and FLP genes and of the ORI, STB, IR1 and IR2 sites of two-micron DNA as well as small "FLP recognition target" (FRT) sites, located near the center of each inverted repeat (IR) at which the FLP recombinase acts, is maintained. Optionally, the restriction site is chosen such that the D gene of two-micron DNA is kept intact, too. Suitable restriction sites are, for example, the unique PstI site located within the D gene and the unique HpaI and SnaBI sites located outside of all of said genes and sites. However, it is likewise possible to insert the expression cassette and further components (cf. below) at different (such as two) restriction sites, especially those mentioned above, within two-micron DNA.

Preferably, the expression plasmids according to the invention include one or more, especially one or two, selective genetic markers, e.g. a marker for yeast and a marker and (except for symmetric two-micron like hybrid vectors) an origin of replication for a bacterial host, especially *Escherichia coli*.

As to the selective gene markers, any marker gene can be used which facilitates the selection for transformants due to the phenotypic expression of the marker gene. Suitable markers are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA3, LEU2, LYS2, HIS3 or TRP1 gene.

As the amplification of the expression plasmids is conveniently done in a prokaryote, such as *E. coli*, a prokaryote, e.g. *E. coli*, genetic marker and a prokaryote, e.g. *E. coli*, replication origin are included advantageously. These can be obtained from corresponding prokaryotic plasmids, for example *E. coli* plasmids, such as pBR322 or a pUC plasmid, for example pUC18 or pUC19, which contain both prokaryotic, e.g. *E. coli*, replication origin and genetic marker conferring resistance to antibiotics, such as ampicillin.

A suitable vector for transforming yeast cells is plasmid pRM 9.1.4 as deposited with the bSM and having the accession number DSM 9271.

Further preferred vector molecules are pRM11.1.4 as deposited with the DSM and having the accession number DSM 9272;

pRM5.1.5 as deposited with the DSM and having the accession number DSM 9270;

pRM4.1.4 as deposited with the DSM and having the accession number DSM 9269; and pRM3.1.10 as deposited with the DSM and having the accession number DSM 9268.

The vector may also be selected from pHE175, pHE175R, pHE177 and pHE177R as disclosed in the experimental part below.

According to a further embodiment of the present invention a method of preparing a tryptase inhibitor is provided, comprising the steps of a) obtaining an extract of a leech, preferably of the medicinal leech *Hirudo medicinalis*, and b) purifying the extract by dialysis and column chromatography.

Preferably the crude extract is dialyzed against a buffer of low ionic strength. Subsequently the dialyzed extract is purified by cation exchange chromatographie, bio-specific chromatography, as for example anhydrotrypsin-sepharose affinity chromatography, and a further cation exchange chromatography step. Further experimental details are illustrated in the experimental part below. Modifications of the claimed process can easily be designed by a person of ordinary skill which are still encompassed by the scope of the present invention.

The invention also refers to methods of preparing recombinant tryptase inhibitor and to recombinant tryptase inhibitors obtainable by these methods. According to one preferred embodiment this method comprises a) transforming a prokaryotic or eukaryotic host with a vector as defined above;

b) inducing the expression of the tryptase inhibitor encoding sequence;

c) recovering the expression product; and optionally d) removing from the obtained product peptide fragments not required for tryptase inhibitor activity and/or optionally renaturing the product.

The coding sequence may also be expressed applying a suitable transcription translation system, as for example the S30 transcription translation system.

According to another embodiment of the present invention prokaryotic and eukaryotic hosts transformed with a vector encoding a tryptase inhibitor, and variants and mutants thereof are provided.

Suitable hosts are of prokaryotic or eukaryotic origin. Examples are bacterial, fungal, plant or insect cells. preferred hosts are bacterial and fungal cells such as *E. coli* or fungi like *Saccharomyces cerevisiae, Aspergillus niger, Aspergillus nidulans* or *Neurospora crassa*.

Preferred yeast strains are those mentioned above, e.g. strains of *S. cerevisiae* which have been cured of the endogenous two-micron plasmid ("cir° strains") and especially strains which are singly or multiply deficient in yeast proteases; and/or, in the case the CUP1 promoter is used, yeast strains containing 1–3 additional copies of the chromosomal CUP1 gene.

A wide variety of proteinases, like those mentioned, have been characterized in the yeast *Saccharomyces cerevisiae* [Achstetter et al. (1985)]. Mutants lacking activity of most of these proteases have been isolated and studied biochemically. The consequences of the absence of certain proteases were elucidated and some properties proved to be useful for the production of heterogeneous proteins. The proteases which are lacking in the yeast strains according to the invention do not perform indispensible functions in the cell metabolism; therefore mutations which completely destroy the activity of these proteins are not lethal. For example, the yeast strain lack one or more proteases selected from the group of carboxypeptidases yscα-, yscB, yscA, yscY and yscS. Methods for the production of such yeast strains are described, for example, in EP-A-40170 and EP-A-341215.

The transformation of host with the hybrid plasmids according to the invention may be accomplished according to methods known in the art.

A preferred embodiment refers to a eukaryotic host derived from *S. cerevisiae* S-78 as deposited with the DSM and having the accession number DSM 9273 and to variants and mutants thereof capable of producing a tryptase inhibiting molecule.

According to another preferred embodiment of the present invention pharmaceutical compositions are provided, comprising a tryptase inhibiting amount of a polypeptide as defined above, prepared from leech extracts or obtained for example by expression of a recombinant tryptase inhibitor encoding gene, optionally in combination with a pharmaceutically acceptable carrier or diluent.

These compositions can be used in particular in the case of the indications mentioned herein, if they are administered, e.g. parenterally (such as intravenously, intracutaneously, intramuscularly or subcutaneously), orally, by inhalation or topically. The dosage depends essentially on the specific method of administration and on the purpose of the treatment or prophylaxis. The size of the individual doses and the administration programme can best be determined based on an individual assessment of the relevant case. The methods required to determine the relevant factors are familiar to the expert. Normally, in the case of injection, the therapeutically active quantity of the compounds according to the invention is in the dosage range of approximately 0.005 to approximately 1 mg/kg of body weight. The range from approximately 0.01 to approximately 0.05 mg/kg of body weight is preferred.

Administration is by intravenous, intramuscular or subcutaneous injection. consequently, depending on the method of application, pharmaceutical preparations for parenteral administration contain approximately 0.5 to approximately 10 mg of the compound according to the invention per individual dose. In addition to the active ingredient, these pharmaceutical compositions usually also contain a buffer, e.g. a phosphate buffer, intended to keep the pH value between approximately 3.5 and 7, and, furthermore, sodium chloride, mannitol or sorbitol in order to adjust isotonicity. They can be in freeze-dried or dissolved form, wherein the solutions can advantageously contain an antibacterial preserving agent, e.g. 0.2 to 0.3% of 4-hydroxybenzoic acid methyl ester or ethyl ester.

A preparation for topical application can be in the form of an aqueous solution, lotion or jelly, an oily solution or suspension or a fatty or, particularly, emulsion ointment. A preparation in the form of an aqueous solution is obtained, e.g. by dissolving the substance according to the invention or a therapeutically useful salt thereof in an aqueous buffer solution of pH 4 to 6.5 and, if desired, adding one or more further substance thereto. The concentration of the active ingredient is approximately 0.08 to approximately 1.5 mg, preferably 0.25 to 1.0 mg, in approximately 10 ml of a solution or 10 g of a jelly.

An oily form of application for topical administration is obtained, e.g. by suspending the substance according to the invention or a therapeutically useful salt thereof in an oil, optionally with the addition of swelling agents, such as aluminium stearate, and/or surface-active agents (surfactants) the HLB value (hydrophilic-lipophilic balance) of which is less than 10, such as fatty acid monoesters of polhydric alcohols, e.g. glycerol monostearate, sorbitan monolaurate, sorbitan monostearate or sorbitan monooleate. A greasy ointment is obtained, e.g. by suspending the substance according to the invention or the salts in a spreadable greasy base, optionally with the addition of a surfactant having an HLB value of less than 10. An emulsion ointment is obtained by trituration of an aqueous solution of the substance according to the invention or the salts in a soft spreadable greasy base with the addition of a surfactant, the HLB value of which is less than 10. All of these forms of topical application can also contain a preserving agent. The concentration of the active ingredient is approximately 0.08 to approximately 1.5 mg, preferably 0.25 to 1.9 mg in approximately 10 g of the matrix.

This invention also relates to the bioanalytical use of the compounds according to the invention and the salts thereof for the analytical determination of trypase and the preparations serving to this end, containing the substances according to the invention, e.g. solid mixtures and above all solutions, in particular aqueous solutions. In addition to a specific quantity or concentration of the substances according to the invention (also in the form of a salt), these can also contain inert adjuvants, e.g. those mentioned above with reference to the injection preparations, which have, e.g. a stabilising and/or preserving function.

According to a further embodiment the present invention is concerned with the use of a tryptase inhibitor as defined above in diagnosing functional tryptase and mast cell related disorders. Especially preferred is the use for preparing pharmaceutical compositions for the treatment of asthma, intestinal lung disease, arthritis, periodontal disease, allergic disorders, blood clotting disorders, skin disorders and psoriasis.

EXPERIMENTAL PART

1. MATERIALS a) Leech Extracts: Extracts from the medical leech *Hirudo medicinalis* were a gift from Plantorgan, Germany. The leech extracts may also be prepared on the basis of the disclosure of EP-A-0 207 956 and the references cited therein.

b) Enzymes and Substrates: Proteases were obtained as follows: bovine trypsin, porcine pancreatic kallikrein, and porcine pancreatic elastase (Sigma; Deisenhofen, Germany); human factor Xa (Boehringer Mannheim; Mannheim, Germany); human neutrophil elastase, human thrombin, human urokinase, and bovine chymotrypsin (Medor; Herrsching, Germany); human plasmin, and human plasma kallikrein (Kabi; Essen, Germany); human cathepsin G (Calbiochem; Bad Soden, Germany).

Tryptase was purified from human lung tissue to apparent homogeneity using a modification of described methods [Smith Hougland, 1984; Schwartz Lewis Austen, 1981; Harvima Schechter, 1988].

The following substrates were purchased: Bz-Ile-Glu-Gly-Arg-pNA (Novabiochem; Bad Soden, Germany); Suc-Ala-Ala-Ala-pNA (Bachem; Heidelberg, Germany); D-Pro-Phe-Arg-pNA, and D-Val-Leu-Arg-pNA (Kabi; Essen, Germany); Suc-Val-Pro-Phe-pNA, and Pyr-Gly-Arg-pNA (Medor; Herrsching, Germany); MeO-Suc-Ala-Ala-Pro-Val-pNA (Sigma; Munich, Germany). Tos-Gly-Pro-Arg-pNA was obtained from Boehringer Mannheim, Medor, and Sigma. (Tos=tosyl; Suc=succinyl; pNA=p-nitroanilide).

Vasoactive intestinal peptide (VIP) was purchased from Calbiochem (Bad Soden, Germany), and bovine lung heparin from Sigma. Bdellin B was a gift from E. Fink (Klinische Chemie und Klinische Biochemie, Chirurgische Klinik, LMU; Munich, Germany).

c) Column materials: SP-Sephadex®, cyanogen bromide-activated Sepharose® 4B and Mono S® HR 5/5 were obtained from Pharmacia (Freiburg, Germany).

Anhydrotrypsin was prepared from trypsin, affinity-purified by a modification of the methods described by Ako [Ako Foster Ryan, 1972], and immobilised onto cyanogen bromide-activated Sepharose 4B according to the guidelines of Pharmacia.

d) Cell culture: Media, foetal calf serum, and antibiotics were obtained from Biochrom (Berlin, Germany). The human keratinocyte cell line HaCaT [Boukamp Petrussevska, 1988] was obtained from N. Fusenig, German Cancer Research Center (DKFZ; Heidelberg, Germany). [Methyl-$^3$H]thymidine was purchased from Amersham Buchler (Braunschweig, Germany).

2. METHODS 2.1. Purification of the Leech-derived Tryptase Inhibitor a) Chromatography on SP-Sephadex®: Leech extract (~3.5 g) was dissolved in deionised water (77 ml) and dialysed against 20 mM NaP (pH 8.0) over night at 4° C. The dialysed material was applied onto a SP-Sephadex® column (1.6×20 cm) equilibrated with the same buffer. The column was washed at a flow rate of 1 ml/min until the optical density (280 nm) of the effluent reached baseline, and eluted with 20 mM NaP, 500 mM NaCl (pH 8.0). Fractions containing inhibitory active material were collected and pooled.

b) Affinity-chromatography on anhydrotrypsin-Sepharose®: The pooled material from the cation exchange chromatography (~20 ml) was applied onto an anhydrotrypsin-Sepharose column (1.6×3.6 cm) equilibrated with 20 mM NaP (pH 8.0). Approximately 90% of the inhibitory active material applied was bound; the remainder in the flow-through was collected for rechromatography. After extensive washing of the column (~10 column volumes) elution was started by addition of 100 mM KCl/HCl (pH 2.1) at a flow rate of 0.3 ml/min. Fractions were collected and neutralised immediately by addition of 1 M Tris. The pooled eluate was dialysed against 20 mM NaP (pH 8.0) over night at 4° C.

c) Chromatography on Mono S®: The dialysed eluate from the affinity chromatography was bound on a Mono S cation exchange column (0.5×5 cm) equilibrated with 20 mM NaP (pH 8.0). The column was washed with the same buffer (~20 ml), and eluted using a gradient from 60 to 240 mM NaCl in 50 column volumes at flow rate of 1 ml/min. Fractions containing inhibitory active material were pooled (~5 ml), aliquoted, and stored at −20° C.

2.2. Standard Analytical Methods a) Protein Assay: Protein concentrations were determined using the bicinchoninic acid procedure [Smith Krohn, 1985] with bovine serum albumin as standard.

b) Electrophoresis: Electrophoretic analysis of reduced and denatured protein was performed using 10–20% SDS-polyacrylamide gradient gels as described by Laemmli [Laemmli, 1970]. Proteins were detected after silver staining [Heukeshoven, 1985].

c) HPLC: Samples (~1 nmol) were loaded onto a Lichrospher RP 8 reversed phase column (120×4 mm; Merck) and eluted using a linear gradient from 0% to 30% acetonitrile in 0.1% TFA at a flow rate of 1 ml/min.

d) sequence analysis:

Reduction and S-β-pyridylethylation: S-β-pyridylethylation was carried out essentially as described by Friedman et al. [Friedman Krull, 1970]. The inhibitor (1–2 nmol) was dissolved in 100 μl buffer (6 M guanidinium-HCl, 0.25 M Tris-HCL, 1 mM EDTA, 5% (v/v) β-mercaptoethanol; pH 8.5) and incubated overnight at room temperature. After addition of 5 μl 4-vinylpyridine and incubation for 90 min, the reaction was stopped by acidification with formic acid. The S-pyridinethylated inhibitor was desalted by reversed phase chromatography on an Aquapore RP 300 column (2.1×30 mm; Applied Biosystems, Pfungstadt, Germany).

Oxidation of the inhibitor: A mixture of formic acid (45 μl) and hydrogen peroxide (30%; 5 μl) was preincubated for 1 h at RT. Thereafter, the inhibitor (1–2 nmol) was dissolved in this mixture. After incubation for 1 h at 4° C., the reaction was stopped by dilution with 1 ml deionised water and lyophylisation.

Fractionation: The inhibitor (1 nmol) was incubated with trypsin and/or chymotrypsin (both sequencing grade; Boehringer Mannheim) in 100 μl of 1 M ammoniumhydrogencarbonate buffer (pH 8.0) for 14 h at 37° C. An enzyme/inhibitor ratio of 1:40 was used. The reaction was terminated by acidification with formic acid, and fragments were separated by HPLC.

Amino acid sequence analysis: Automated amino-acid sequencing was performed using a gas-phase sequencer 473A (Applied Biosystems, Weiterstadt, Germany).

e) sequence comparison: The MIPSX-database (Martinsrieder Institut fur Proteinsequenzen am Max-Planck-Institut für Biochemie, Martinsried, Germany) was searched using the Lipman & Pearson fast protein searching algorithm FASTP [Lipman Pearson, 1985]. Alignments were optimised using CLUSTAL [Higgins Sharp, 1988].

f) Amino acid analysis: Samples of oxidised inhibitor were hydrolysed under vacuum in 5.7 M hydrochloric acid at 110° C. for 20 h and analysed on a Biotronik LC 5000 high performance analyser system (Puchheim, Germany).

g) Determination of the molecular mass: The molecular mass of the HPLC-purified inhibitor (50 μM) was determined using a tandem quadrupole instrument API III (Sciex, Thornhill, Ontario, Canada). The instrument was calibrated with the ammonium adduct ions of polypropylene glycol.

h) Inhibitory activity: During the purification procedure the inhibitor was followed by measurements of its effect on the amidolytic activity of tryptase. Therefore, samples were incubated with tryptase (0.59 nM) in 50 mM Tris/HCl (pH 7.6), 150 mM NaCl, 50 μg/ml bovine lung heparin, and 0.1% (w/v) bovine serum albumin for 25 min at 37° C. The assay was started by addition of the substrate tos-Gly-Pro-Arg-pNa at a final concentration of 0.1 mM. The released nitroaniline was monitored spectrometrically at 405 nm for 3.5 min using a UVIKON 930 photometer (Kontron; Eching, Germany).

One inhibition unit (IU) was defined as the amount of inhibitor which reduces the substrate hydrolysis by 30%.

i) Titration of the inhibitor: The concentration of inhibitory active leech-derived tryptase inhibitor was determined by titration with trypsin. Therefore, bovine pancreatic trypsin was standardised by active-site titration using p-Nitrophenyl p'-guanidinobenzoate [Chase Shaw, 1970]. The concentration of active inhibitor was calculated assuming a 1:1 interaction between the inhibitor and trypsin.

k) Determination of equilibrium constants: To determine the specificity of the inhibitor, its effect on the amidolytic activity of various serine proteinases (see Tab. 5) was determined. Therefore, proteinases were incubated with the inhibitor (0.2 μM) for 15 and 30 min under the conditions indicated in Tab. 5. The residual enzyme activity was measured after addition of a suitable substrate.

Equilibrium dissociation constants ($K_i$) for the complexes of the inhibitor with individual proteases were determined essentially as described by Bieth [Bieth, 1980]. Briefly, increasing concentrations of the inhibitor were incubated with a constant concentration of the enzyme; the time necessary to reach equilibration of the enzyme-inhibitor complex was determined for each protease in preliminary experiments. Substrate was then added, and the residual enzyme activity measured. $K_i$-values were calculated by fitting the steady state velocities to the equation for tight binding inhibitors [Morrison, 1969] using non-linear regression analysis.

l) Coagulation assay: The prothrombin time according to Quick and the partial thromboplastin time were measured using an Amelung KC 10 coagulometer (Lemgo, Germany) and the reagent sets from Behringwerke AG (Marburg, Germany) according to the guidelines of the manufacturers.

m) Cleavage of vasoactive intestinal peptide (VIP): Tryptase (4.8 nM) was preincubated with different concentrations of the leech-derived tryptase inhibitor in 100 mM Tris (pH 7.4), 140 mM NaCl, 50 μg/ml heparin at 37° C. for 25 min. Vasoactive intestinal peptide (VIP; 24 μM, final concentration) was then added. After incubation for additional 1 to 10 min, the reaction was stopped by acidification with acetic acid. The remaining VIP and the fragments generated were quantified using HPLC.

n) Growth of human keratinocytes: For growth studies the human keratinocyte cell line HaCaT, a spontaneously transformed cell line maintaining characteristics of differentiated keratinocytes [Boukamp Petrussevska, 1988], was utilised. HaCaT cells were plated in 24-well tissue culture plates (Falcon; Becton Dickinson, Heidelberg, Germany) at a density of $10^4$ cells/cm$^2$ in a medium containing 90% Dulbecco's modified Eagles' medium, 10% foetal calf serum, and 50 μg/ml gentamicin. Cells were incubated at 37° C. in 5% $CO_2$. After 24 h, the cells were washed twice with serum-free Dulbecco's modified Eagles' medium, and fresh serum-free medium containing 7.8 μg/ml heparin alone or medium containing the agonists and/or the inhibitor was added. After 48 h, the cells were washed two times again, and fresh serum-free medium containing 1 μCi/ml ³H-thymidin was added. After additional 2 h, the cells were washed three times with ice-cold Dulbecco's PBS, and incorporated ³H-thymidin was precipitated by 10% trichloroacetic acid. After solubilisation of the precipitate in 0.1 N NaOH, 1% SDS, the incorporated radioactivity was determined by liquid scintillation counting (beta counter model LS 1800, Beckman Instruments, Munich, Germany). For growth studies other keratinocyte cell lines may be applied as well.

EXAMPLE 1

Figure 2:
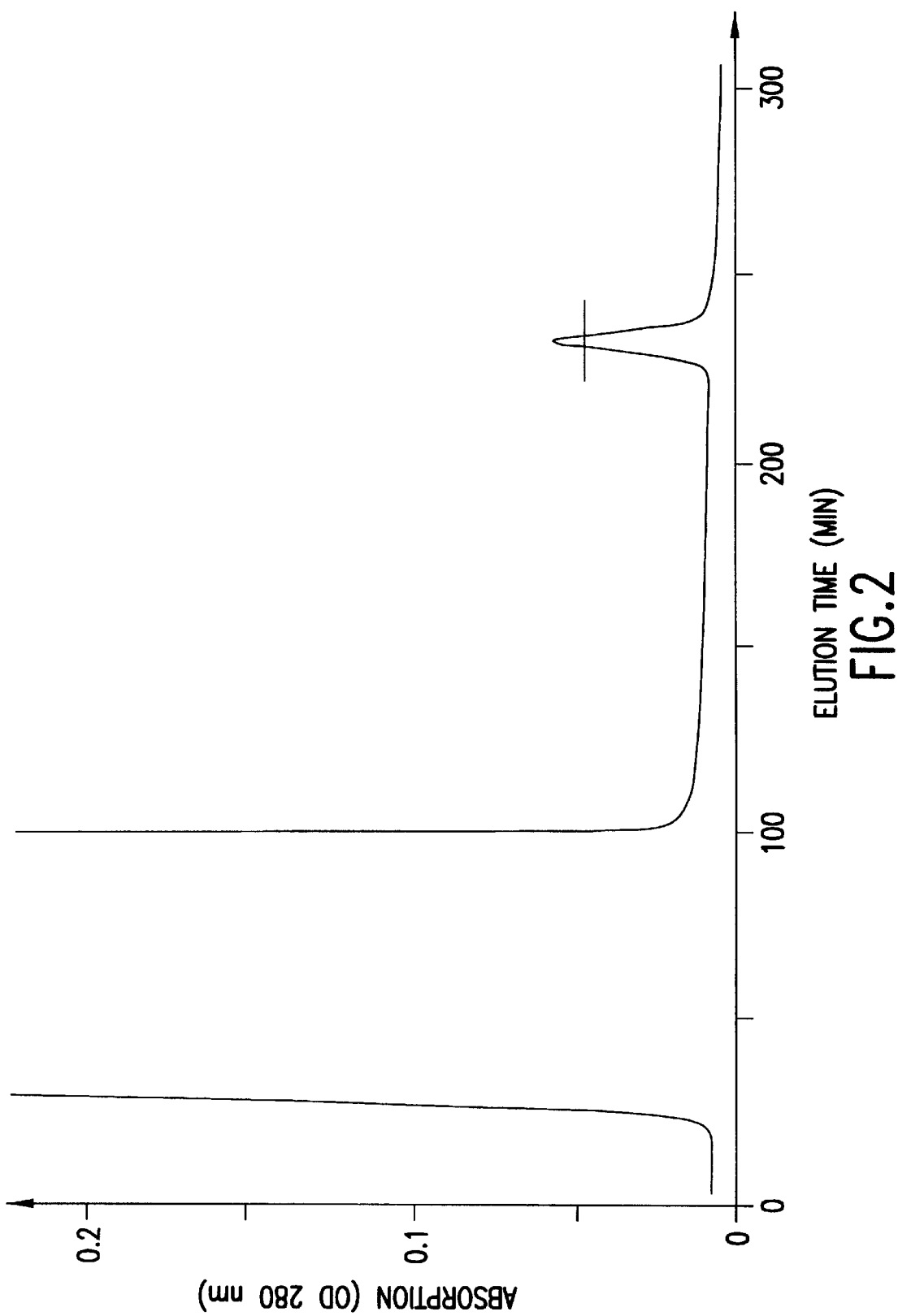
FIG. 2: Affinity-chromatography of the leech-derived tryptase inhibitor using anhydrotrypsin-Sepharose. The pooled eluate from the SP-Sephadex chromatography was applied, the column washed extensively and eluted with 100 mM KCl/HCl (pH 2.1). Fractions containing inhibitory active material (marked with a bar) were collected and neutralised immediately by addition of 1 M Tris.
Figure 3:
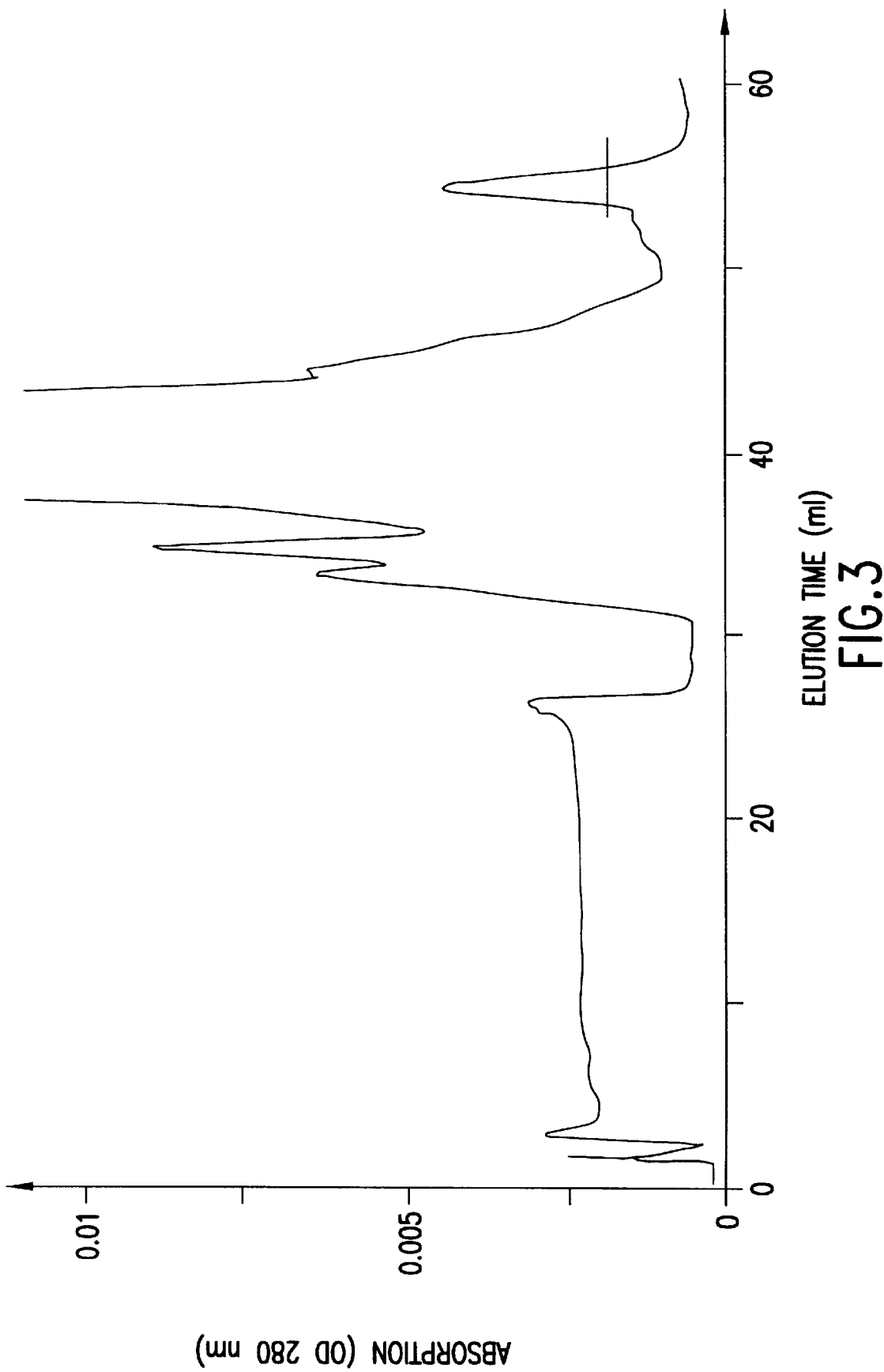
FIG. 3: Cation-exchange chromatography of the leech-derived tryptase inhibitor using a Mono S FPLC column. After dialysis against 20 mM NaP (pH 8.0) the pooled eluate from the anhydrotrypsin affinity-chromatography was applied, the column washed, and eluted using a linear gradient from 60 to 240 mM NaCl. The fractions containing inhibitory active material (marked with a bar) were pooled.

Isolation of the Leech-derived Tryptase-inhibitor 3.5 g of lyophilised leech extract was dissolved in water, dialysed against 20 mM NaP (pH 8.0), and applied onto a SP-Sephadex® cation exchange column (see Method Section). The bulk of the protein (~98%) and of the trypsin-inhibitory activity was found in the flow-through, whereas the leech-derived tryptase inhibitor was bound to the column. After elution of the column with 500 mM NaCl (FIG. 1), the inhibitor was separated from non-trypsin inhibiting proteins by subsequent affinity-chromatography on anhydrotrypsin-sepharose (FIG. 2). Final purification was achieved by Mono S® cation-exchange chromatography (FIG. 3). The data of the isolation procedure are summarised in Table 1.

TABLE 1

Purification of the leech-derived tryptase inhibitor.

| Purification step | Volume [ml] | Protein [mg] | Activity [IU] | Specific activity [IU/mg] | Yield [%] | Purification (fold) |
|---|---|---|---|---|---|---|
| Dialysis | 91.5 | 2311 | 124000 | 50 | — | — |
| SP-Sephadex | 19.7 | 35.8 | 103000 | 2890 | 83 | 58 |
| Anhydro-trypsin-Sepharose | 15.2 | 2.11 | 47100 | 22300 | 38 | 446 |
| Dialysis | 14.5 | 1.75 | 36300 | 20700 | 29 | 414 |
| Mono S | 4.5 | 0.08 | 9910 | 122000 | 8 | 2440 |

3.5 g of lyophilised leech extract was used as starting material. One inhibitory unit (IU) was defined as the amount of inhibitor reducing the amidolytic activity of tryptase by 30% (see Methods).

Figure 4:
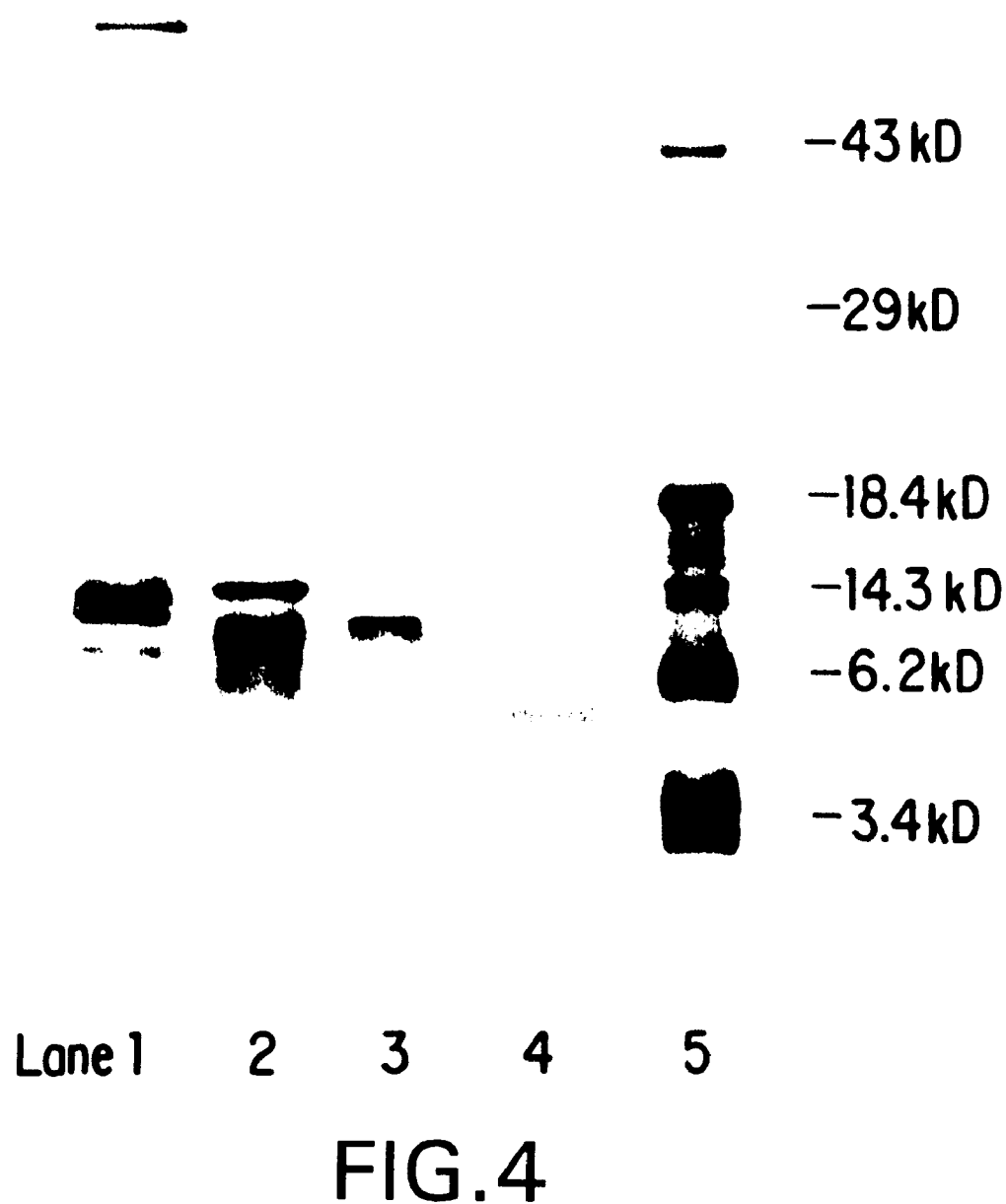
FIG. 4: SDS-PAGE of the isolated leech-derived tryptase inhibitor under reducing conditions. Lane 1=dialysed leech extract; lane 2=eluate from the SP-Sephadex column; lane 3=eluate from the anhydrotrypsin affinity-chromatography; lane 4=eluate from Mono S cation exchange chromatography. The molecular weight markers (lane 5) are from top to bottom: ovalbumin (43 kD), carbonic anhydrase (29 kD), β-lactoglobulin (18.4 kD), lysozyme (14.3 kD), bovine trypsin inhibitor (6200 D), and insulin β-chain (3400 D).
Figure 5:
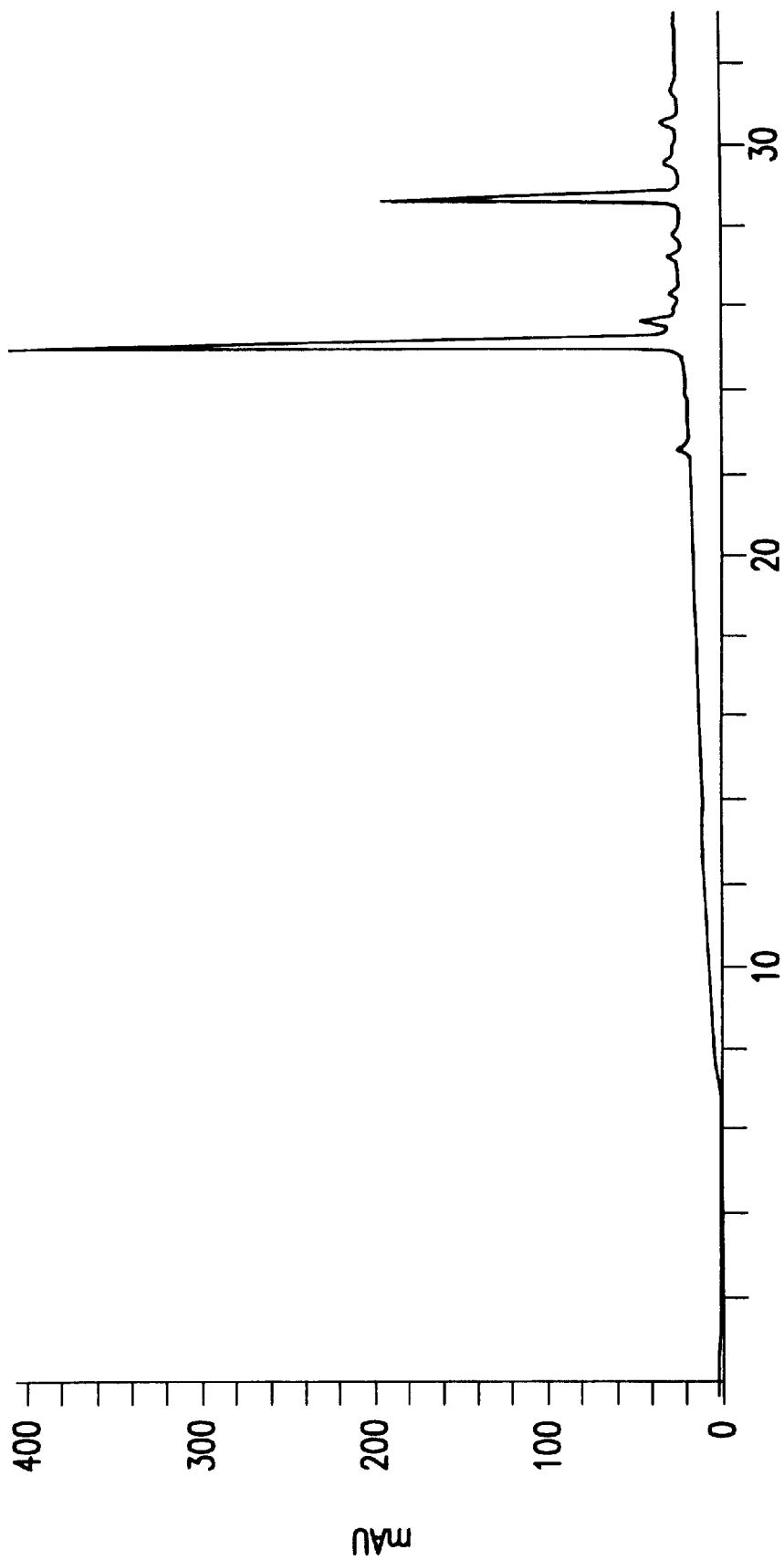
FIG. 5: Reversed phase HPLC of the isolated leech-derived tryptase inhibitor. The elution time and the absorption of the effluent at 206 nm are given on the abscissa and the ordinate, respectively. The two peaks demonstrate the presence of at least two forms.
Figure 6:
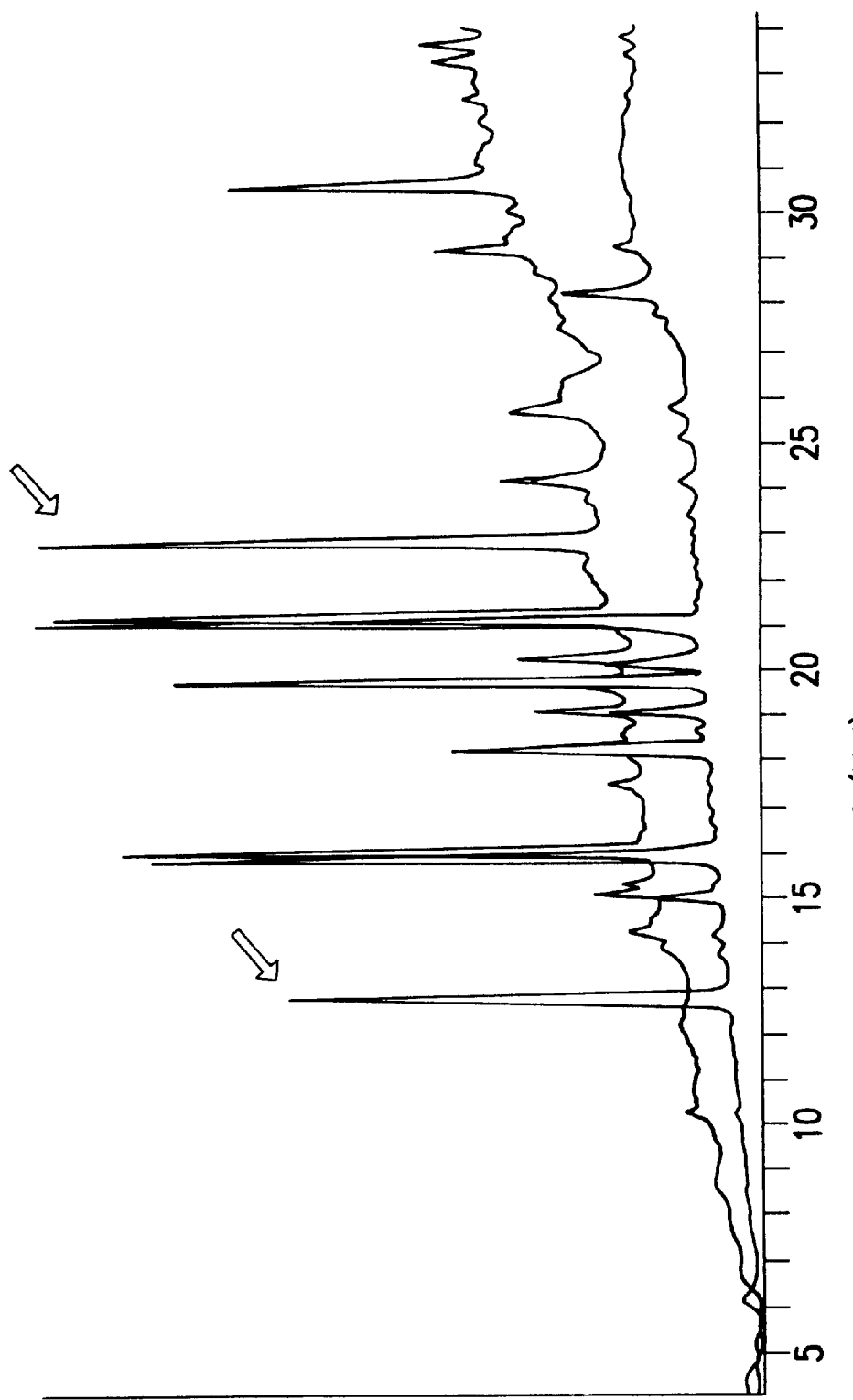
FIG. 6: Tryptic fragmentation of the two species of the leech-derived tryptase inhibitor separated by reversed phase HPLC (see FIG. 5). Lower tracing: HPLC-tracing of the tryptic digest of the peak eluting at 25 min in FIG. 5; Upper tracing: HPLC-tracing of the tryptic digest of the peak eluting at 29 min. The elution profiles differ only in the peaks representing the C-termial peptides (marked by arrows).
Figure 7A:
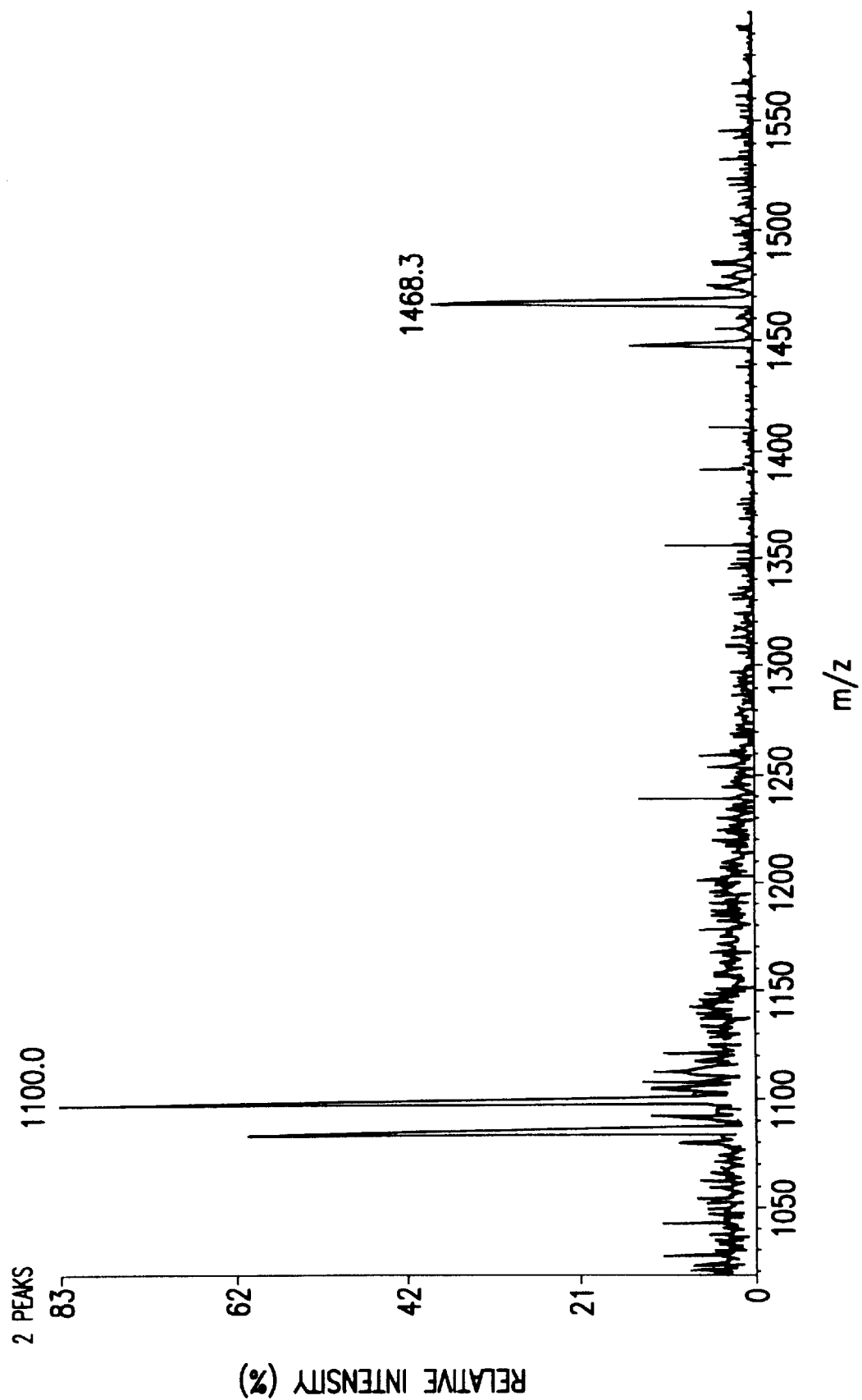
FIGS. 7A and 7B: Mass spectroscopy of the two species of the leech-derived tryptase inhibitor separated by HPLC (see FIG. 5). a) The mass spectrum of the HPLC peak eluting at 25 min demonstrates the presence of 2 forms with a mass of 4340 (form A; left peaks) and 4396 (form B; right peaks), respectively. b) The mass spectrum of the HPLC peak eluting at 29 min shows a third form (form C) with a mass of 4738.
Figure 7B:
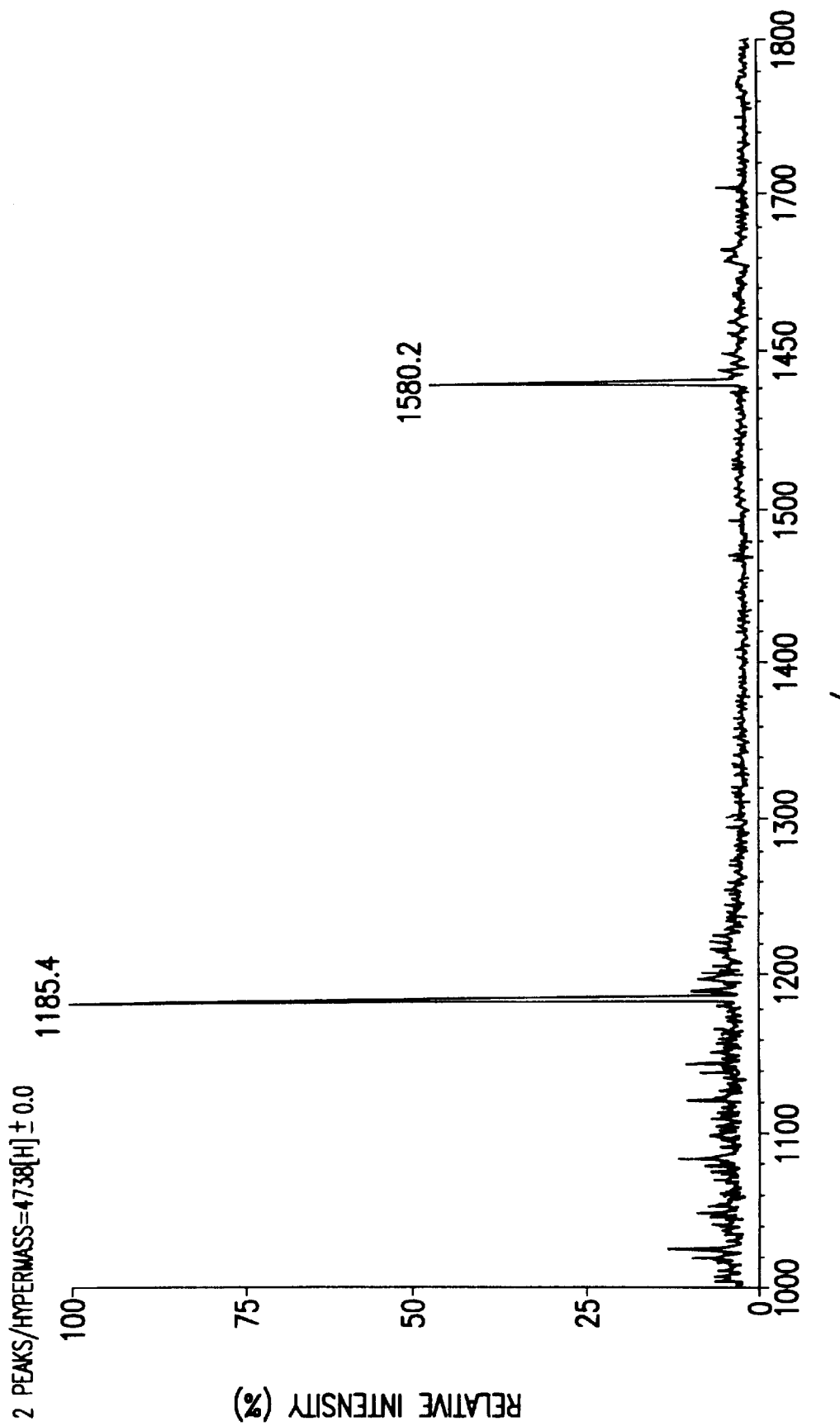

The isolated leech-derived tryptase inhibitor was homogeneous according to SDS-PAGE and N-terminal sequence analysis (FIGS. 4 and 8). However, two species were separated by reversed phase HPLC (FIG. 5). Subsequent amino acid sequencing after tryptic fragmentation, amino acid analysis, and mass spectroscopy (Tab. 2, FIG. 6 and 7) demonstrated that the two species comprise three forms differing only in their C-terminal sequence. Thus, forms B (43 aa) and C (46 aa) differ from the shortest form A (42 aa) by a C-terminal extension of -GLY and -GLY-ILE-LEU-ASN, (the last 4 amino acids of SEQ ID NO:3) respectively. The results obtained for the 3 forms are compared in Tab. 3.

TABLE 2

Amino acid analysis of the two species of the leech-derived tryptase inhibitor separated by HPLC (see FIG. 5).

| Amino acid | Form A/B[1] | Form C |
|---|---|---|
| Asx | 3.49 (3) | 4.18 (4) |
| Thr | 2.17 (2) | 2.22 (2) |
| Ser | 4.76 (5) | 4.86 (5) |
| Glx | 1.43 (1) | 1.26 (1) |
| Gly | 5.3 (4/5)[2] | 5.62 (5) |
| Ala | 3.43 (3) | 3.18 (3) |
| Cys | 5.68 (6) | 5.24 (6) |
| Val | 2.82 (3) | 2.94 (3) |
| Ile | 3.15 (3) | 4.19 (4) |
| Leu | 1.08 (1) | 2.03 (2) |
| Tyr | n.d. (1) | n.d. (1) |
| Lys | 5.03 (5) | 5.00 (5) |
| Arg | 1.7 (2) | 1.74 (2) |
| Pro | 3.01 (3) | 3.81 (3) |

The values given in brackets are the values calculated from the amino acid sequence. [1]) Forms A and B have not been separated; [2]) The sequence of the forms A and B contain 4 and 5 glycins, respectively; n.d. not determined

TABLE 3

Summary of the characterisation of the three forms of the leech-derived tryptase-inhibitor.

| | Form A | Form B | Form C |
|---|---|---|---|
| C-terminal Sequence | CPT | CPTG | CPTGILN |
| Molecular mass determined by mass spectroscopy | 4340 | 4396 | 4738 |
| Molecular mass calculated from the sequence[1] | 4341 | 4398 | 4738 |
| Elution time on reversed phase HPLC (see FIG.5) | 25 min[2] | | 29 min |
| Elution time of the C-terminal peptide of the tryptic digest (see FIG.6) | 13 min[2] | | 23 min |
| Inhibitory activity | +[2] | | + |

[1])assuming three disulphide bonds
[2])Forms A and B have not been separated

The N-terminal 35 amino acid residues of the leech derived inhibitor were determined by sequencing the native inhibitor. The primary structure was completed and verified using overlapping peptides generated after modification and tryptic and/or chymotryptic fragmentation (FIG. 8).

Sequence comparisons demonstrate that the leech-derived tryptase inhibitor is a non-classical Kazal-type serine proteinase inhibitor. The highest degree of similarity was found to Bdellin B [Fink Rehm, 1986]; in the sequence section common to both inhibitors (amino acids 1–40), 19 of 40 (47.5%) amino acids are identical (Tab. 4). Despite the high sequence identity to the leech-derived tryptase inhibitor, Bdellin B, an inhibitor also isolated from the medical leech, does not affect tryptase (unpublished observations).

TABLE 4

Comparison of the amino acid sequences of the
leech-derived tryptase inhibitor and Bdellin B-3
[Fink Rehm, 1986].

```
Tryptase-   1     5    10    5    20    5    30    5    40
Inhibitor   KKVCACPKILKPVCGSDGRTYANSCIARCNGVSIKSEGSC
Bdellin     DTECVCTKELHRVCGSDGVTYDNECLATCHGASVAHDHAC
B-3         .. *.*.* *..****** **.*.*.* *.*.*.  . .*

Figure 9:
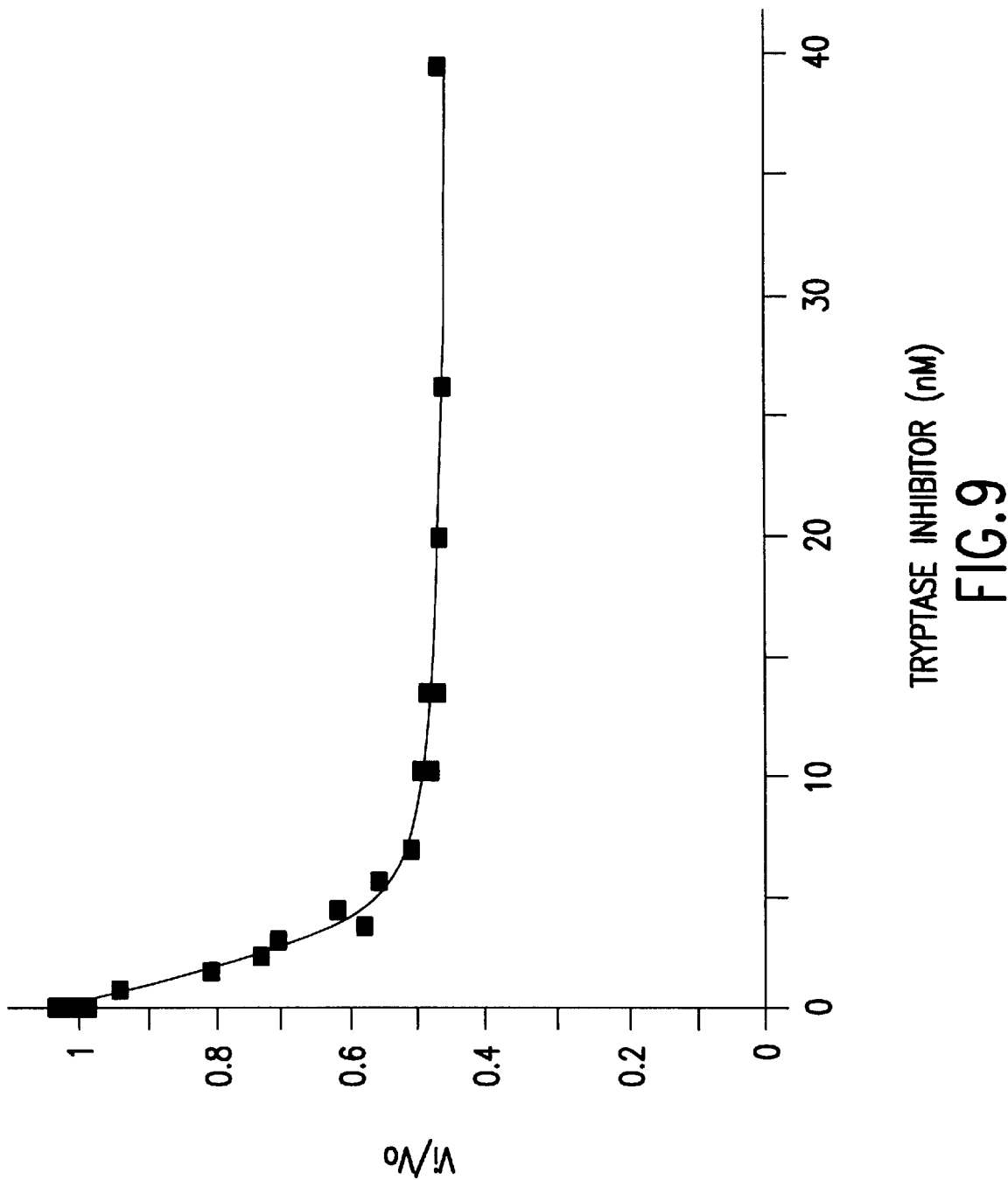
FIG. 9: Inhibition of human tryptase by the leech-derived tryptase inhibitor. Tryptase (0.59 nM) was preincubated with increasing concentrations of the leech-derived tryptase inhibitor (0–40 nM) at 37° C. for 25 min, and the reaction was initiated by the addition of substrate tos-Gly-Pro-Arg-pNa. The resulting steady state velocities were measured over 3.5 min. The values given are the quotient of the velocity in the presence of the inhibitor divided by the velocity in the absence of the inhibitor.

Tryptase-
Inhibitor   --------------PT
``` maximal inhibition of 50% was observed (FIG. 9). Thus, most likely due to steric hindrance, the inhibitor blocks only two of the four catalytic subunits of the tryptase tetramer, leaving the other two subunits accessible to the small substrate. The interaction of the inhibitor with the first two tryptase-subunits can be described mathematically as a tight binding inhibition with a $K_i$ of ~1.4 nM for the complex. The leech-derived tryptase-inhibitor is highly specific and inhibits only trypsin and chymotrypsin with affinities similar to that for tryptase (Tab. 5). In contrast, the $K_i$-values for the complexes with other proteinases are at least 200 times higher.

TABLE 5

Specificity of the Leech-derived tryptase inhibitor. ([1]at 0.2 μM; [2]$K_i$ for the inhibition of two of the four subunits of the tryptase-tetramer; ni, no inhibition at 0.2 μM; nd, not determined)

| Enzym | Substrate | Buffer | Enzym-concentration [nM] | Substrate-concentration [mM] | Pre-incubation | $K_m$ [mM] | $K_i$ app [nM] | $K_i$ [nM] |
|---|---|---|---|---|---|---|---|---|
| Tryptase (human) | Tos—Gly—Pro—Arg—pNA | 50 mM Tris/HCl pH 7.6 150 mM NaCl, 0.1% BSA 50 ug/ml BLH, 0.5% DMSO | 0.59 | 0.1 | 25 min, 37° C. | 0.38 | 1.8 | 1.4[2] |
| Trypsin (bovine) | Tos—Gly—Pro—Arg—pNA | 50 mM Tris/HCl pH 7.8 0.1% Triton, 1% DMSO | 0.45 | 0.1 | 20 min, 37° C. | 0.02 | 4.7 | 0.9 |
| Chymotrypsin (bovine) | Suc—Val—Pro—Phe—pNA | 100 mM Tris/HCl pH 7.8 0.1% Triton, 1% DMSO | 1.1 | 0.25 | 15 min, 37° C. | 0.04 | 137 | 20 |
| Plasmin (human) | Tos—Gly—Pro—Lys—pNA | 50 mM Tris/HCl pH 7.8 0.1% Triton, 1% DMSO | 2.7 | 0.14 | 30 min, 37° C. | nd | 30% inhibition[1] | nd |
| Tissue-Kallikrein (porcine) | D—Vat—Leu—Arg—pNA | 100 mM Tris/HCl pH 8.2 0.1% Triton | 31 | 0.12 | 30 min, 25° C. | nd | 14% inhibition[1] | nd |
| Thrombin (human) | Tos—Gly—Pro—Arg—pNA | 100 mM Tris/HCl pH 8.2 0.1% Triton, 7% DMSO | 1.8 | 0.14 | 30 min, 25° C. | nd | 12% inhibition[1] | nd |
| Cathepsin G (human) | Suc—Val—Pro—Phe—pNA | 100 mM Tris/HCl pH 7.5 500 mM NaCl 0.1% Triton, 1% DMSO | 16 | 0.25 | 30 min, 25° C. | nd | 11% inhibition[1] | nd |
| Plasma-Kallikrein (human) | D—Pro—Phe—Arg—pNA | 50 mM Tris/HCl pH 7.8 2% DMSO | <<87 | 0.2 | 30 min, 37° C. | nd | ni[1] |  |
| Faktor Xa (human) | Bz—Ile—Glu—Gly—Arg—pNA | 100 mM Tris/HCl pH 8.2 0.1% Triton, 4% DMSO | 10 | 0.8 | 30 min, 25° C. | nd | ni[1] |  |
| Pankreatic Elastase (porcine) | Suc—Ala—Ala—Ala—pNA | 100 mM Tris/HCl pH 7.5 500 mM NaCl 0.1% Triton, 2% DMSO | 72 | 2 | 30 min, 25° C. | nd | ni[1] |  |
| Neutr. Elastase (human) | MeO—Suc—Ala—Ala—Pro—Val—pNA | 100 mM Tris/HCl pH 7.5 500 mM NaCl 0.1% Triton, 2% DMSO | 4.2 | 1 | 30 min, 25° C. | nd | ni[1] |  |
| Urokinase (human) | Pyr—Gly—Arg—pNA | 100 mM Tris/HCl pH 0.2 0.1% Triton, 2% DMSO | 34 | 0.9 | 30 min, 25° C. | nd | ni[1] |  |

TABLE 4-continued

Comparison of the amino acid sequences of the
leech-derived tryptase inhibitor and Bdellin B-3
[Fink Rehm, 1986].

```
Bdellin     EGHEEHHVDEHGEDHD
B-3
```

(* = identical residues; . = homologues amino acids)

EXAMPLE 2

Specificity of the Leech-derived Inhibitor

The leech-derived tryptase-inhibitor inhibits human tryptase in a concentration-dependent fashion. Using the tripeptide-nitroanilid tos-Gly-Pro-Arg-pNa as a substrate, a

EXAMPLE 3

Biologic Characterisation

To determine whether the leech-derived tryptase inhibitor affects the cleavage of a biologically relevant substrate by tryptase, its effect on the breakdown of vasoactive intestinal peptide (VIP) was measured. At a concentration of $4 \times 10^{-7}$ M, the inhibitor reduced the breakdown of VIP by 66% (FIG. 10). Thus, the inhibitor blocks not only the tryptase-induced cleavage of the peptide nitroanilid substrate tos-Gly-Pro-Arg-pNA (see Example 2), but also that of a biologically relevant substrate.

Tryptase not only cleaves soluble proteins, but also directly interacts with cells activating cellular functions such as the growth of fibroblasts and keratinocytes. To determine whether the leech-derived tryptase inhibitor blocks these cellular effects of tryptase, its effect on the tryptase-induced growth of cultured human keratinocytes was studied. In the absence of the inhibitor, tryptase ($10^{-9}$M) markedly stimulated the growth of keratinocytes, increasing their $^3$H-tymidin incorporation to 182±6% of the control. The leech-derived tryptase inhibitor did not significantly affect the baseline growth suggesting a lack of cytotoxic effects (Tab. 6).

TABLE 6

Effect of the leech-derived tryptase inhibitor on the proliferation of the human keratinocyte cell line HaCaT.

| Condition | Growth rate (% of control) |
| --- | --- |
| Medium alone | 100 |
| + Inhibitor $10^{-7}$M | 96 ± 3 |
| + Tryptase | 182 ± 6 |
| + Tryptase + Inhibitor $10^{-7}$M | 115 ± 6 |
| + Tryptase + Inhibitor $10^{-8}$M | 120 ± 2 |

Growth rates were calculated as the incorporation of $^3$H-thymidine in the presence of the agonist and/or inhibitor expressed as a percentage of the incorporation in medium alone. Data are given as mean±SEM, n≧2.

The inhibitor greatly reduces the tryptase-induced ($10^{-9}$ M) cell growth without significant effect on the proliferation under baseline conditions. Thus, the inhibitor nearly completely blocks of the biologic effect of tryptase without cytotoxic side effect.

However, the inhibitor significantly reduced the tryptase-induced proliferation, reducing the $^3$H-tymidin incorporation to 115±5% and 120±2% of the control at a concentration of $10^{-7}$M and $10^{-8}$M, respectively. As this $^3$H-tymidin incorporation is similar to that caused by $10^{-11}$M tryptase (118±4%), the data suggest that the inhibitor blocks the cellular effect of tryptase by approximately 99%.

Finally, the influence of the leech-derived tryptase inhibitor on the prothrombin time (according to Quick) and the partial thromboplastin time were measured to determine whether it interferes with the blood coagulation. At a concentration of $10^{-7}$M, the inhibitor has no significant effect on both parameters (Tab. 7). Thus, the leech-derived tryptase inhibitor does not significantly inhibit any of the proteases involved in the blood coagulation cascade.

TABLE 7

Effect of the leech-derived tryptase inhibitor on the blood coagulation.

| | Quick | Partial Thromboplastin Time |
| --- | --- | --- |
| Control | 89% | 37.3 sec |
| Tryptase-Inhibitor | 91% | 37.1 sec |

The inhibitor (100 nM) does not affect the prothrombin time according to Quick and the partial thromboplastin time, demonstrating that the enzymes involved in the coagulation cascade are not inhibited.

EXAMPLE 4

Pharmaceutical Preparation Containing the Tryptase Inhibitor for Parenteral Administration A solution prepared in accordance with Example 1 is dialysed against a 0.9% strength NaCl solution. The concentration of the solution is then adjusted to 1 mg/ml or 10 mg/ml by concentration or by dilution with the same NaCl solution. These solutions are sterilised by ultrafiltration (membranes having 0.22 µm pores).

The sterilised solutions can be used for intravenous administration.

EXAMPLE 5

Preparation of Recombinant Tryptase Inhibitor 5.1. Materials

All chemicals used were obtained from Sigma, St. Louis, USA; Merck, Darmstadt, FRG; Serva, Heidelberg, FRG; Biomol, Hamburg, FRG; Roth, Karlsruhe, FRG; Braun, Melsungen, FRG; Dianova, Hamburg, FRG; Promega, Madison, USA. Restriction endonucleases and DNA-modifying enzymes were purchased from Boehringer, Mannheim, FRG; New England Biolabs, Beverly, USA and Pharmacia-Biotech, Freiburg, FRG. Adenosine-5'-α [$^{35}$S]-thiotriphosphate was obtained from Amersham Buchler, Braunschweig, FRG.

Bacto-tryptone, Bacto-peptone, Bacto yeast nitrogen base (without amino acids, w/o), Bacto yeast extract and Bacto-agar were from Difco, Augsburg, FRG. As culture media we used 2×YT [Sambrook et al, 1989]; YPD (10 g Bacto yeast extract, 20 g Bacto peptone, 20 g glucose, pH 6.0); YED (20 g Bacto yeast extract, 20 g glucose, 6.7 g $NaH_2PO_4$, pH 6.0) and SD+ (6.7 g Bacto nitrogen base (w/o), 20 g glucose, 6.7 g $NaH_2PO_4$, 9 mg L-leucine, pH 6.0).

Oligonucleotides were purchased from MWG-Biotech, München, FRG or synthesized by Dr. S. Modrow, München, FRG.

Vectors and strains: The *E. coli* pUC cloning vector was from Pharmacia Biotech Europe GmbH, Freiburg. The *E.coli-S.cerevisiae* shuttle and expression vector pVT102U/α and the yeast strain S-78 were kindly provided by T. Vernet, Montreal, CAN and by C.-W. Chi and Y.-S. Zhang both Shanghai, China [Lit. Vernet et al, Chen et al). *E. coli* TG1 ((lac-pro), supE, thi, hsdD5/F'traD36, proA$^+$B$^+$, lacI$^q$, lacZM15) was from Amersham-Buchler, Braunschweig,FRG,; *E.coli* JM105 (thi, rspL, endA, sbcB15, hspR4, (lac-proAB) F'traAB proAB, lacI$^q$, lacZM15); and *E. coli* HB101 (F$^-$, pro$^-$, leu$^-$, thi$^-$ lacY, Sm$^r$, endoI$^-$, recA$^-$, $r_k^-$, $m_k^-$) were from Deutsche Stammsammlung Braunschweig, FRG.

The standard techniques of molecular cloning were performed according to Sambrook et al. [Sambrook et al.,1989] and to M.-D. Rose et al. [Rose et al., 1990].

5.2. Standard Analytical Methods a) SDS-PAGE and isoelectric focussing (IEF) SDS-PAGEs of the proteins were performed with 15–25% polyacrylamide gels following the procedure of Laemmli [Laemmli, 1970]. The gels were either self-prepared and run in a conventional apparatus or in the PhastSystem (Pharmacia, Sollentuna, Sweden). Isoelectric focussing was also done with the PhastSystem using the isoelectric focussing calibration kit pH 3–10.

b) EPLC analysis, amino acid sequencing

Usually 2–3 nmol of protein were analysed by reversed phase-HPLC as detailed previously [Auerswald et al., 1991. The N-termini were sequenced with a gas-phase sequencer 473A (Applied Biosystems GmbH, Weiterstadt, FRG) following the instructions of the manufacturer.

c) Determination of the protein concentrations

To determine the protein concentration the Pierce BCA* Protein Assay with BSA as standard protein [Smith et al., 1985] was used. $A_{280nm}$ (1%) was calculated for recombinant LDTI-C using the $A_{280}$ values for aromatic residues and cystines of Mach et al. [1992]: $A_{280}$ (1%)=3.46, and for protein mixtures $A_{280}$ (1%)=1.

d) Trypsin inhibition assay

The concentration of inhibitorily active material and the specific inhibitory activity of rLDTI-C was determined indirectly by measuring the residual trypsin activity using the following conditions described by Chase and Shaw, 1970. Test buffer: 0.05M Tris-HCl pH7.6, 150 mM NaCl. 0.1% (v/v) Triton X-100, 600 pM trypsin; 100 $\mu$M Tos-Gly-Pro-Arg-p-NA.

e) Determination of $K_i$ values

Equilibrium dissociation constants ($K_i$) for the complexes of rLDTI-C with trypsin and tryptase were determined essentially as described previously [Bieth, 1980].

5.3. Construction of the Synthetic LDTI-C Gene.

Figure 11A:
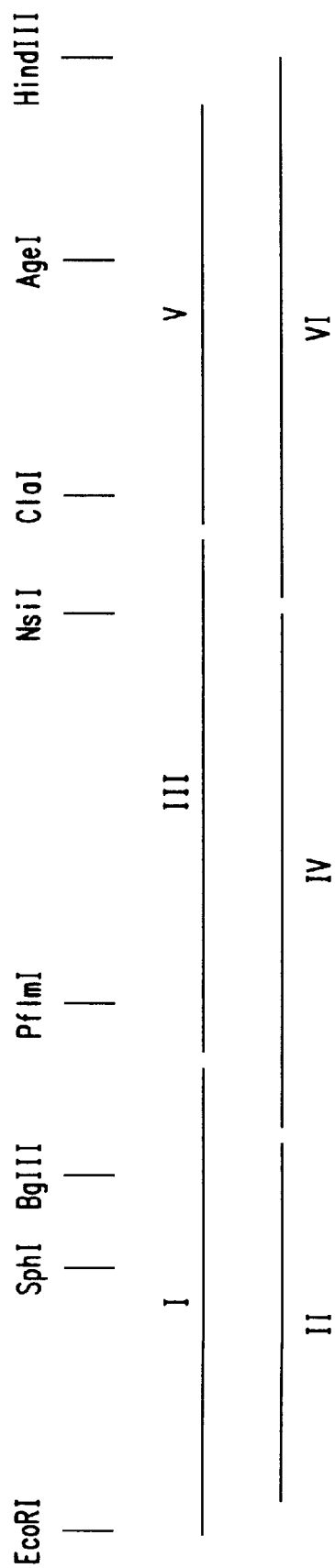
Figure 11C:
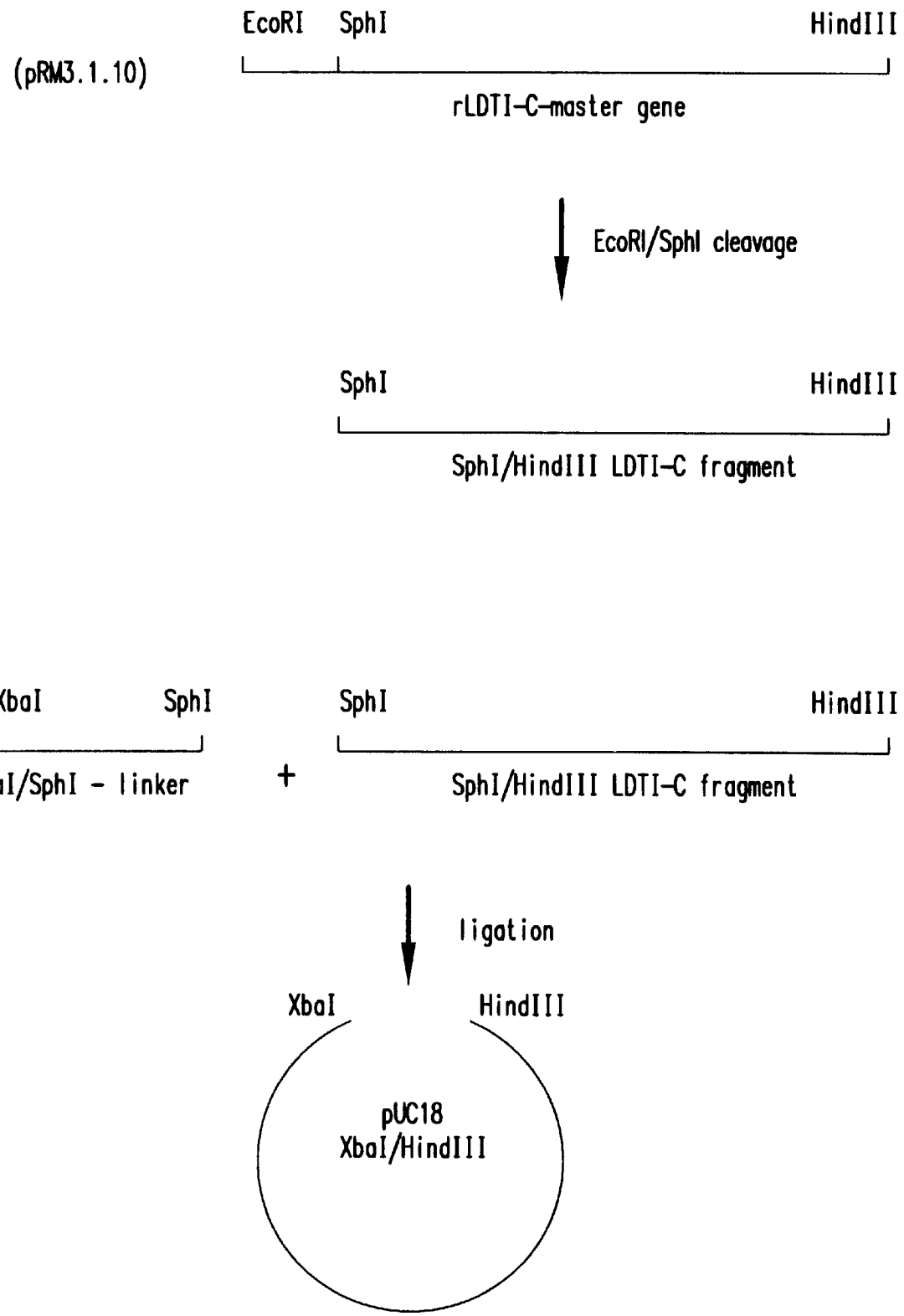

A synthetic gene coding for a recombinant homologue of LDTI form C was designed and constructed as outlined in FIG. 11. The DNA sequence was selected on the basis of the amino acid sequence of natural tryptase inhibitor by assistance of the GCG sequence analysis software [UWGCG, Devereux et al., 1984] with the *E.coli* and *S.cerevisiae* codon usages for strongly expressed genes [Bennetzen and Hall, 1982].

The 5'—OH ends of the internal oligonucleotides were phosphorylated using T4 polynucleotide kinase before hybridisation. All six oligonucleotides, 200 pmol each, were heated 5 minutes to 95° C. Hybridization was achieved during cooling down to room temperature within 8 hours. After phenol extraction and ethanol precipitation, internal nicks were ligated by T4 ligase (Boehringer), according to the manufacturers protocol. The material was separated by gel electrophoresis on a low melting agarose (5%) and a 149 bp long fragment was purified using the MERMAID isolation kit from Dianova, Hamburg.

5.4. Construction of Cloning Vector pRM3.1.10.

The DNA fragment obtained according to 5.3. was ligated into vector pUC18 cut with EcoRI/HindIII (molar ratio of vector:fragment, 1:20). Competent *E.coli* TG1 cells were transformed with the ligation mixture and recombinant clones were selected. DNA sequencing was performed using the M13/pUC (–40) sequencing primer, a 17mer, and the reverse sequencings primer (–48), a 24 mer. Vector pRM3.1.10 (FIG. 15) containing the designed sequences of rLDTI-C was used for further experiments.

5.5. In vitro Production and Cytoplasmic Expression in *E. coli* a) The synthetic LDTI-C gene and the expression vector pASK 40 [Skerra et al., 1991] were cleaved separately with EcoRI and HindIII, purified and ligated. Modified pASK 40 was designated pRM4.1.4 (FIG. 16). The pRM4.1.4 DNA was analysed by an *E.coli* S-30 coupled in vitro transcription translation system, from Promega with S-35 cysteine following the instructions of the manufacturers. The in vitro transcription translation of vector pRM4.1.4 with a commercially available S-30 *E.coli* lysate showed two major radioactive labelled protein bands with app. MW of 7 kDA and 5 kDa (data not shown). The other strong band detected, seems to be β-lactamase (app. MW of 31 kDa). The 7 kDA protein band is interpretated as the uncleaved fusion protein containing the ompA signal sequence and LDTI-C (theoret. MW 7038 Da) whereas the 5 kDa protein (theoret. MW 5015 Da) band seems to be the cleaved and expected [ANS] LDTI-C which is prolongated by three amino acid residues.

b) For cytoplasmic expression the synthetic LDTI-C gene was ligated after a fill-in reaction into pGEX-3X (Pharmacia) cleaved with SmaI. The resulting vector was named pRM 11.1.4 (FIG. 17) and the resulting host strain is *E.coli* 1314 Cytoplasmic glutathione-S-transferase-LDTI-C fusion proteins were found as insoluble inclusion bodies, with *E.coli*. 1314 (HB 101 with pRM11.1.4, data not shown).

5.6. Construction of Expression Vector pRM 9.1.4

For the expression experiments with yeast the modified alpha mating secretion system pVT102U/α ]Vernet et al., 1987) was selected in which Trichosanthes trypsin inhibitor, a small serine proteinase inhibitor of the squash family was expressed successfully [Chen et al., 1992]. Within this system the recombinant inhibitor was correctly folded, cleaved from the signal sequence, protected from proteolytic degradation and it could be purified in two or three steps from yeast fermentation broth.

In order to use the shuttle vector pVT102U/α, the rLDTI-C gene had to be modified first. The LDTI-C gene (FIG. 11) was mutated by substituting the EcoRI/SphI cassette with a XbaI/SphI linker cassette. The sequence of this XbaI/SphI linker is CTAGATAAAAGAAAGAAG-GTTTGCGCATGV (SEQ ID NO:22). It codes for the C-terminal end (FIG. 11*c*) of the alpha mating type signal sequence containing a cleavage site for the KEX2 signal peptidase (Lys Arg) and the N-terminus of LDTI. The modified LDTI-C gene was assembled via a three fragment ligation using the XbaI/SphI linker cassette, the SphI/HindIII LDTI-C fragment and the XbaI/HindIII cleaved pUC18 vector (molar ratio 10:5:1). After transformation of *E.coli* TG1 recombinant clones were screened by restriction analysis and DNA sequencing using the M13/pUC (–40) primer (Biolabs) and the M13/pUC/–48) reverse primer (Biolabs) (CGCAGTAGCGGTAAACG) (SEQ ID NO:24. The new vector pRM 5.1.5 (FIG. 12*a*) carried the expected sequence and the XbaI/HindIII fragment including the rLDTI-C gene was ligated into XbaI/HindIII cleaved pVT102U/α. The resulting expression vector pRM 9.1.4 (FIG. 12*b*) was isolated and used to transform *S.cerevisiae* strain S-78 according to the method of Becker and Guarante [Becker and Guartante, 1991].

5.7. Expression in *Saccharomyces cerevisiae*

Analytical rLDTI-C expression experiments using yeast strain H005 (S-78 with pRM9.1.4) were carried out with Fernbach flasks (180–220 rpm, 28° C.; pre-culture for 3 days with 100 ml SD(+) media and main cultures for 4 days with 900 ml fresh YED-media). At each day cell density ($OD_{700}$) was determined, pH was adjusted to 6.0 with 1M NaOH, 10 ml yeast extract stock solution 50% and 30 ml 50% (w/v) glucose were added and the inhibition of trypsin was determined.

After transformation of competent S-78 strains with pRM9.1.4 expression of rLDTI was detected. The broth of cultivated recombinant yeast cells showed remarkable trypsin inhibition The concentrated supernatant gave a protein pattern with the strongest band migrating at an app. MW of 5000 Da after SDS-PAGE (see FIG. 13, lane 2).

The recombinant material was isolated preparatively from culture broth of *S. cervisiae* cultivated in 1 liter shaker-flasks for 96 h. After this time the growth curve of yeast cells reached an $OD_{700}$ of 22.0. Trypsin inhibitory activity was detected after two days and increased parallel to the biomass.

The yeast broth was harvested (6000 g, 20 min, 4° C.) after 96 h cultivation and the supernatant was filtered, first through a 0,16 $\mu$m membrane and then through a crossflow membrane with a 3 kDa cut-off (Filtron Omega Minisette, Filtron, Karlstein, FRG)). The buffer was exchanged by diafiltration to 20 mM $NaH_2PO_4$ pH 8.2. The material was purified by cation-exchange chromatography (Fractogel EMD SO$_3^-$ 65o (S) column 150-10; Merck), flow rate 3 ml/min, elution buffer 20 mM NaH$_2$PO$_4$, pH8.2, 500 mM NaCl.

The data of a representative purification are summarized in Table 8.

TABLE 8

Results of a typical purification of r LDTI form C from *Saccharomyces cereviseae* culture supernatant

| Purification step | Volume (ml) | Total protein (mg) | Active material (mg) | Specific activity (%) | Yield (%) |
|---|---|---|---|---|---|
| culture supernatant | 1000 | 5620 | 10.6 | 0.1 | 100 |
| culture supernatant, 0.16 μm filtration | 965 | 4600 | 5.2 | 0.1 | 49 |
| retentate, 3K-membrane | 125 | 850 | 4.6 | 0.5 | 43 |
| Fractogel EMD SO$_3$ main fractions | 21 | 5 | 3.2 | 59 | 30 |

Figure 13:
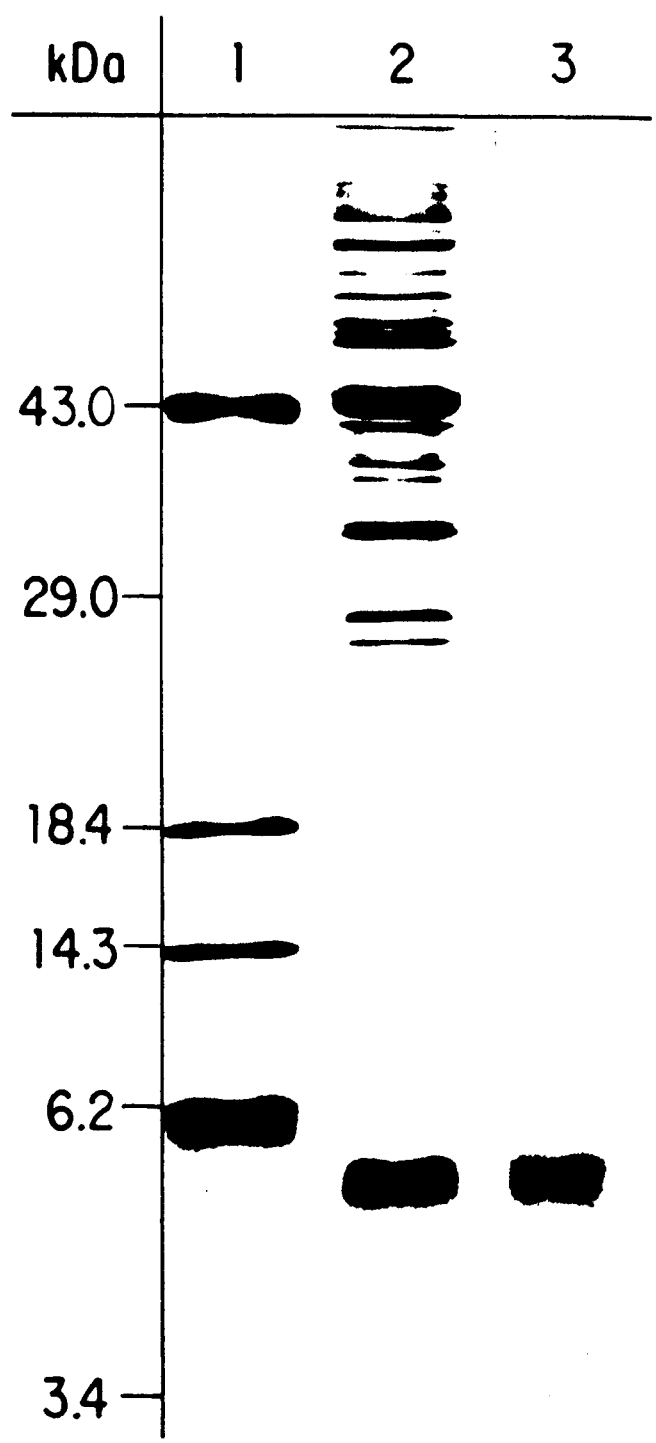
FIG. 13: SDS/PAGE analysis of fermentation supernatant and purified rLDTI form-C. lane 1=low-molecular mass-markers; lane 2=fermentation supernatant of yeast strain HOO5 after 96 hours of cultivation (80 μl); lane 3=purified rLDTI-form C (2 μg).
Figure 14:
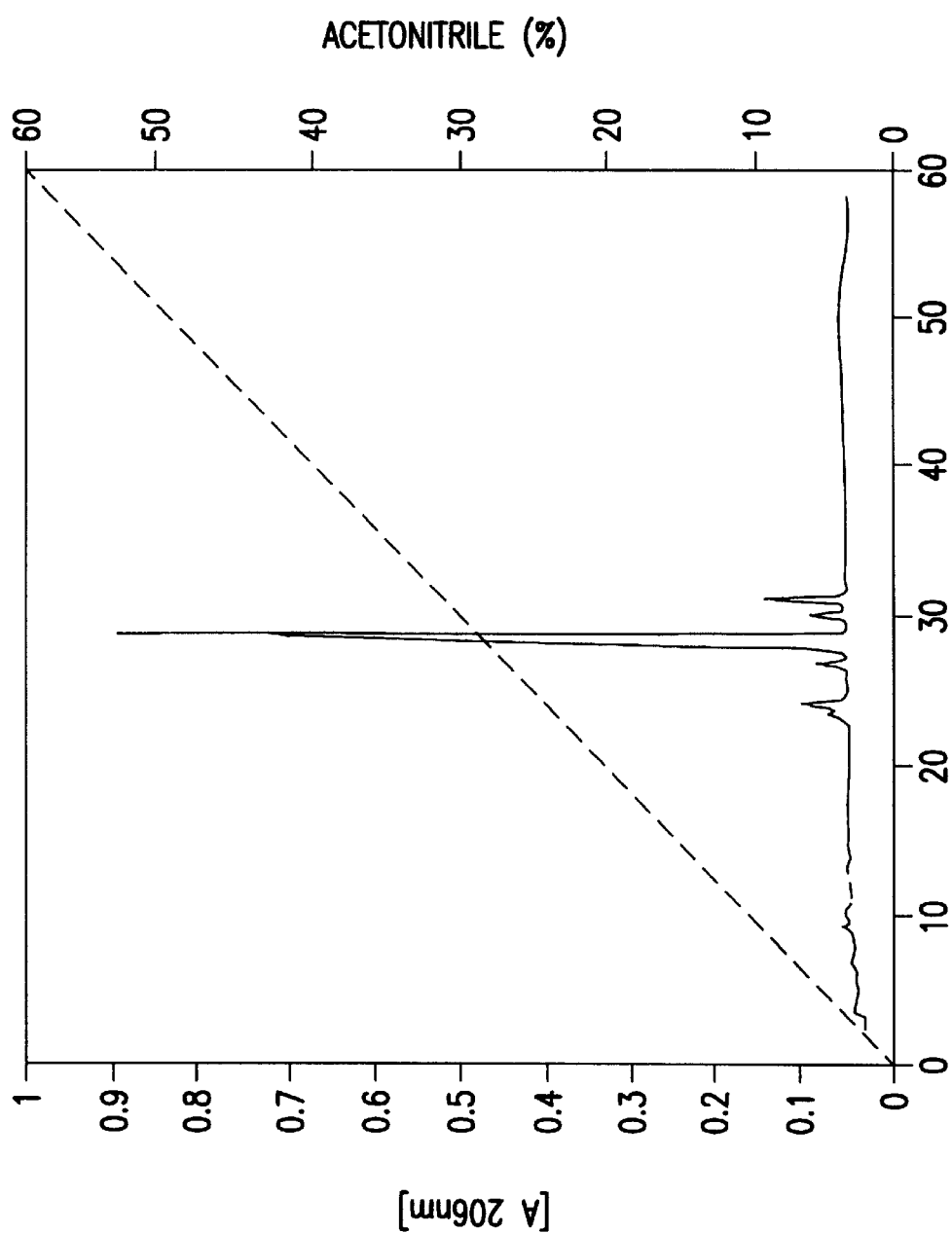
FIG. 14: HPLC analysis of purified rLDTI form-C. Reverse phase HPLC on a RP 18 column was performed with 7,4 nmol (35 μg) purified inhibitor. A linear gradient of 0–60% (by vol.) acetonitrile formed from 0,1% (by vol.) trifluoroacetic acid in acetonitrile and 0,1% (by vol.) trifluoroacetic acid was used. The flow rate was adjusted to 1.0 ml/min and the absorbance in the effluent was monitored at 206 nm.

Total protein was estimated applying the Pierce assay (bovine serum albumin as standard); active material was calculated from trypsin inhibitory assays; yield is given as percentage of isolated material;

From one liter fermentation broth 3 mg rLDTI-C were obtained. The SDS-PAGE of this material showed a homogeneous but relatively broad band migrating at an app. MW of 5000 Da (FIG. 13, lane 3). About 85% of rLDTI-C eluted as a sharp peak at 28% acetonitrile when analysed by RP18 HPLC. The amino acid sequencing of peak 1 (FIG. 14) revealed the expected N-terminus KKVCACPK. But small heterogeneities were observed after RP-HPLC and a different N-terminus was identified (peak 2) starting with 11 additional amino acids of C-terminal part of alpha factor signal peptide (FIG. 14).

This demonstrates that the endogeneous KEX 2 protease of yeast did cleave with high accuracy after LysArg, the recognition site of the signal peptidase KEX2, and still in front of the two N-terminal amino acid residues LysLys of LDTI. Isoelectric focussing with the PhastSystem demonstrated that the isoelectric point of rLDTI was above pH 10.

The determined inhibition constants of the complexes tryptase-LDTI-C and trypsin-LDTI-C are similar to those with natural LDTI. The measured specific trypsin inhibitory activity of 60% is comparable to other recombinant inhibitors.

rLDTI-C inhibits human tryptase in a fashion similar to the naturally occuring leech-derived tryptase inhibitor: using the tripeptide-nitroanilid tos-Gly-Pro-Arg-pNa as a substrate, a maximal inhibition of ~50% was observed, and a K$_i$ of 1.9 nM was calculated for the complex between tryptase and rLDTI-C.

EXAMPLE 6

Construction of pFBY166 pFBY166 is a pUC18 derived plasmid that contains a 1085 bp BamHI fragment. This fragment contains the CUP1 promoter fused to the ATG of the α-factor leader, a stuffer fragment and the α-factor terminator. The precise way the fusions were engineered enable the insertion of ORF (open reading frame) containing fragments either at the ATG by using the EcoRI site, after the signal sequence by using a PstI site or after the α-factor leader sequence by insertion after the BglII site. The ORF to be expressed should ideally have a SalI site at their 3' end to facilitate fusion to the terminator that is preceded by a SalI site, and have no BamHI sites within their sequence, as cleavage of this plasmid at the two BamHI sites excises the whole expression cassette so that it can easily be cloned into a yeast shuttle vector.

pFBY166 contains a 425 bp BamHI/EcoRI fragment of the CUP1 promoter, corresponding to nucleotides 1080 to 1505 of EMBL GENBANK accession number K02204. The CUP1 promoter allows expression in a copper regulated manner.

The ATG is provided as part of the α-1 factor pheromone signal sequence and leader, nucleotides 293 to 527 of the EMBL GENBANK accession number X01581 followed by the sequence, AGATCTTGC, which positions a BglII site, which is unique in pFBY139, just before the normal position for the LysArg KEX2 cleavage site. If fusions are required to just a signal sequence this can be achieved by using the unique PstI site which is present within the region encoding the signal sequence. The BglII site is followed by a sequence of no importance as it is always removed when the incoming ORF is cloned into the plasmid between either the EcoRI, PstI or BglII sites and the SalI site which marks the end of the stuffer fragment and the beginning of the α-1 factor pheromone terminator sequences, nucleotides 825 to 1100 of EMBL GENBANK accession number X01581. This is followed immediately by the sequence AATTCGGATCC (SEQ ID NO:23) which encodes the BamHI site that bounds this end of the expression cassette.

This plasmid can be constructed using polymerase chain reaction (PCR) fragments from yeast genomic DNA.

All oligonucleotides used in the PCR reaction are synthesized using an automatic DNA synthesizer. The PCR reactions are carried out in a PCR unit from Perkin Elmer under the following conditions: 20 mM of the oligonucleotides in question are incubated in 0.1 ml buffer (10 mM Tris-HCl, pH 8.3, 50 mM KCl , 1.5 mM MgCl2) with 2.5 units of Taq DNA-polymerase and 0.2 mM of dATP, dCTP, dTTP and dGTP. The reactions are incubated for 30 cycles: 30 sec at 92° C., for 1 min at 42° C. and at 72° C. for 1 min.

The fragment comprising most of the α-factor signal and leader sequences is generated from genomic yeast DNA using the PCR fragments 1 (SEQ ID NO: 10) and 2 (SEQ ID NO: 11):

1. 5' GTGCGAATTCAAAATGAGATTTCCTTCAATTTTTACTGCAG 3'

2. 5' CAAAGTCGACTTTATCCAGCAAGATCTCTTCTTCTTTAGCAGCAATGC 3'

The fragment comprising the α-factor terminator is generated from genomic yeast DNA using the PCR fragments 3 (SEQ ID NO: 12) and 4 (SEQ ID NO: 13):

3. 5' GAAGAGATCTTGCTGGATAAAGTCGACTTTGTTCCCACTGTACTTTTAGC 3'

4. 5' CCGGGGATCCGAATTAATTCTCTTAGGATTCG 3'

The fragment comprising the CUP1 promoter is generated from genomic yeast DNA using the PCR fragments 5 (SEQ ID NO: 14) and 6 (SEQ ID NO: 15):

5. 5' TAGAGGATCCCCATTACCGACATTTGGGCGCTATACGTGC 3'

6. 5' CGACGAATTCACAGTTTGTTTTTCTTAATATCTATTTCG 3' and subsequent cleavage with BamHI and EcoRI.

The fragment comprising most of the α-factor signal and leader sequences and the fragment comprising the α-factor terminator are mixed and reamplified in a PCR reaction with oligonucleotide 1 and oligonucleotide 3 and cut with EcoRI and BamHI. The later amplified fragment and the fragment comprising the CUP1 promoter are cloned into pTZ18R cut with BamHI and treated with bacterial alkaline phosphatase to create pFBY139.

EXAMPLE 7

Construction of pHE 174 Expression of Tryptase Inhibitor Under Control of the Regulated CUP1 Promoter A synthetic gene encoding tryptase inhibitor in preferred yeast codon usage is assembled from 3 synthetic oligonucleotides in a PCR reaction. In addition, the gene is extended at its 5' end to provide for convenient in-frame fusion to the α-factor leader in plasmid pFBY 166.

The following 3 oligonucleotides are synthesized using an automatic DNA synthesizer:

(SEQ ID NO: 16)
1. 5'-AAAGATCTTG CTGGATAAAA GAAAGAAGGT TTGCGCCTGT

CCAAAGATTT TGAAGCCAGT TTGTGGTTCT GACGGTCGTA
   CC-3'

(SEQ ID NO: 17)
2. 5'-ACAAGAACT TCAGACTTAA TAGAAACACC GTTACAACGG
   GCAATACAAG AGTTGGCGTA GGTACGACCG TCAGAACCAC-3'

(SEQ ID NO: 18)
3. 5'-TTGTCGACTC AGTTCAAAAT ACCGGTTGGA CAAGAACCTT

CAGACTTAA-3'

Of these 3 oligonucleotides a 170 bp fragment is assembled in the following polymerase chain reaction (PCR) using the PCR unit from Perkin Elmer and the following conditions:

20 mM of oligonucleotides 1 and 3 and 20 nM of oligonucleotide 2 are incubated in 0.1 ml buffer (10 mM Tris-HCl, pH 8.3, 50 mM KCl, 1.5 mM MgCl2) with 2.5 units of Taq DNA-polymerase and 0.2 mM of dATP, dCTP, dTTP and dGTP. The reaction is incubated for 30 cycles: 30 sec at 92° C., for 1 min at 42° C. and at 72° C. for 1 min.

The 170 bp PCR fragment is isolated over a 2% agarose gel, restricted with BglII and SalI and ligated into BglII and SalI cut pFBY 166 (supra). E. coli HB101 is transformed with the resulting plasmid pHE174. The transformed E. coli strain is designated E. coli/pHE174.

Correct fusion of the PCR fragment to the α-factor leader and correct sequence of the tryptase inhibitor ORF is confirmed by sequencing.

EXAMPLE 8

Construction of pHE 175 and 175R 2 Micron Vectors with the Tryptase Inhibitor Expression Cassette For the expression in yeast pDP34 is used as vector. pDP34 (EP-A-340 170, FIG. 3 therein) is a yeast-E. coli shuttle vector with the ampicillin resistance marker for E. coli and the URA3 and dLEU2 yeast selective markers. It contains the complete 2 micron sequences in the A form and is REP1, REP2 and FLP proficient.

Plasmid pDP34 is digested with BamHI and the sticky ends are dephosphorylated by alkaline phosphatase treatment. pHE174 is digested with BamHI and the 1119 bp fragment containing the complete tryptase inhibitor expression cassette ligated into BamHI-cut pDP 34. E. coli HB 101 is transformed with the resulting plasmids pHE 175 and 175R. Orientation of the insert is tested by digestion with SalI. pHE 175 contains the Tryptase inhibitor expression cassette in a clockwise orientation with respect to dLEU2, pHE 175R in anticlockwise orientation with respect to the dLEU2 marker.

EXAMPLE 9

Construction of pHE 176 The Tryptase Inhibitor ORF Fused to the Invertase Signal Sequence (SUC2)

To provide for an alternative secretion system, the tryptase inhibitor ORF is fused to the signal sequence of the yeast invertase gene SUC2.

The 2 following oligonucleotides are made:

(SEQ ID NO: 19)
1. 5'-TTGTCGACTC AGTTCAAAAT A-3'

(SEQ ID NO: 20)
2. 5'-AAGAATTCAT GCTTTTGCAA GCTTTCCTTT TCCTTTTGGC

TGGTTTTGCA GCCAAAATAT CTGCAAAGAA GGTTTGCGCC

TGTC-3' pHE 174 is used as template DNA for a polymerase chain reaction as described in example 7. 20 ng of template pHE 174 is incubated with 20 mM of the oligonucleotide primers under the experimental conditions as in example 7.

The 214 bp amplified PCR fragment is isolated over a 2% agarose gel, restricted with EcoRI and SalI and ligated into EcoRI and SalI cut vector pFBY 166.

E. coli HB 101 is transformed with the resulting plasmid pHE 176. Correct sequence of the SUC2 signal sequence-tryptase inhibitor fusion is confirmed by sequencing.

EXAMPLE 10

Construction of pHE 177 and pHE 177R 2 Micron Vectors with the Tryptase Inhibitor Expression Cassette with the SUC2 Signal Sequence In analogy to example 8, the 918 bp BamHI fragment containing the tryptase inhibitor expression cassette is excised from pHE 176 by BamHI digestion and inserted into BamHI cut pDP 34. E. coli HB 101 is transformed with the resulting plasmids pHE 177 and pHE 177R. Orientation of the insert is tested by digestion with SalI. pHE 177 contains the tryptase inhibitor expression cassette in a clockwise orientation with respect to dLEU2, pHE 177R in an anticlockwise orientation.

EXAMPLE 11

Construction of Saccharomyces cerevisiae Strain TR 1456

Saccharomyces cerevisiae strain TR1456 is constructed as disclosed in EP-A-341 215. Starting with Saccharomyces cerevisiae strain H449 (DSM 4413, MATa, leu23,112, ura3, prb1 [cir°]), in two subsequent series of experiments the two carboxypeptidases yscα and yscY are removed from strain H449 by disruption of their encoding genes KEX1 and PRC1, respectively. First, the gene encoding yscα, KEX1, is disrupted.

For this purpose, strain H449 is transformed with a DNA fragment encoding the KEX1 gene, with the full URA3 gene inserted in the middle of the KEX1 coding region. Uracil prototrophic transformants are selected and tested for the absence of yscα activity. Next, the URA3 gene inserted at the KEX1 locus is disrupted by transformation with a plasmid containing a disrupted version of the gene, URA3Δ5 (see EP-A-341 215). Transformants which are uracil auxotrophic are selected and in the following step disrupted in their endogenous PRC1 gene coding for the carboxypeptidase yscY. The experiment is carried out in a totally analogous manner as described for the disruption of KEX1. The finally resulting isogenic derivative of strain H449 is called TR1456 and has the following genotype:

TR1456=MATa, leu2–3, 112, ura3, prb1, kex1::ura3, prc1::ura3, [cir°]

EXAMPLE 12

Transformation of Strain TR 1456 with Plasmids pHE 175, 175R, 177 and 177R

The plasmids pHE 175, 175R, 177 and 177R are introduced into the host strains H449 and TR1456, resp., using the transformation protocol described by Hinnen et al. (Proc. Natl. Acad. Sci. USA (1978), 75, 1929). Further details of the procedure are as described in EP-A-341 215. Transformed yeast cells are selected on yeast minimal medium, supplemented with leucine and lacking uracil. Single transformed yeast clones are isolated and referred to as:

Saccharomyces cerevisiae TR 1456/pHE 175
Saccharomyces cerevisiae TR 1456/pHE 175R
Saccharomyces cerevisiae TR 1456/pHE 177
Saccharomyces cerevisiae TR 1456/pHE 177R
Saccharomyces cerevisiae H449/pHE 175
Saccharomyces cerevisiae H449/pHE 175R
Saccharomyces cerevisiae H449/pHE 177
Saccharomyces cerevisiae H449 /pHE 177R

EXAMPLE 13

Secretion of Leech-derived Tryptase Inhibitor by TR 1456 Transformed with Plasmid pHE 177

Cells of Saccharomyces cerevisiae TR 1456/pHE 177 are grown in two subsequent precultures of 20 ml each. The synthetic medium is composed of:

| | |
|---|---|
| 6.7 g/l | Difco Yeast Nitrogen Base (without amino acids) |
| 10 g/l | L-asparagine |
| 1 g/l | L-histidine |
| 20 g/l | glucose |
| 0.02 g/l | L-leucine |

The pH of the medium is adjusted to 5.8. The first preculture is grown for 60 h at 28° C. and 180 r.p.m. The second preculture is inoculated with 2% (v/v) of the first preculture and incubated for 24 h at 28° C. and 180 r.p.m.

The medium of the main culture is composed of:

| | |
|---|---|
| 5 g/l | peptone |
| 10 g/l | yeast extract |
| 20 g/l | glucose |
| 40 g/l | sucrose |
| 3 g/l | ammonium sulfate |
| 2 q/l | potassium dihydrogenphosphate |
| 0.5 g/l | magnesium sulfate heptahydrate |
| 0.1 g/l | sodium chloride |
| 0.1 q/l | calcium chloride |
| $10^{-5}$ g/l | biotin |

The main culture (100 ml medium) is inoculated with about 106 cells/ml and incubated for 72 h at 28° C. and 180 r.p.m.

Immediately following the inoculation, sterile copper sulfate is added at a concentration of 1 mM to the culture.

At the end of the fermentation, aliquots of the culture are taken, the cells are removed by centrifugation and the culture supernatant is analyzed for activity of the leech-derived tryptase inhibitor by titration of the inhibitor with trypsin as described under 2.2. i).

EXAMPLE 14

Analytics of the Leech-derived Tryptase Inhibitor from Fermentation Cultures of Saccharomyces cerevisiae Strain TR 1456/pRE177 Using Reversed Phase HPLC Samples from culture supernatants of strain TR 1456/pHE177 are subjected to HPLC analysis under the following conditions:

A Merck Lichrospher 1000 RP-8 column (4×250 mm, 10 um) is used. Mobile phase A is made from water (Nanopur®, Barnstead) containing 0.1% (v/v) trifluoroacetic acid. Mobile phase B is made from 20% water (Nanopur®, Barnstead) and 80% of acetonitrile (HPLC-grade, Fluka) containing 0.09% (v/v) of trifluoroacetic acid.

Chromatographic separations are performed at a flow rate of 1.5 ml/min running the following gradient (Table 9). The eluents are monitored by absorbance at 214 nm.

TABLE 9

| t (min) | % A | % B |
|---|---|---|
| 0 | 85 | 15 |
| 8 | 85 | 15 |
| 28 | 65 | 35 |
| 34 | 0 | 100 |
| 37 | 0 | 100 |
| 42 | 85 | 15 |
| 46 | 85 | 15 |

One major peak with a retention time of 19.05 min is observed on the chromatogram that is present in strains bearing the inhibitor expression plasmid, but absent in untransformed strains. Further analysis revealed that this peak contains one species of the leech-derived tryptase inhibitor with an apparent Mr of 4738,8 as detected by mass spectroscopy. This value is in good agreement with the calculated Mr value of 4738, pointing to the full-length inhibitor molecule carrying both, the correct N-terminus and C-terminus.

The chemical molecular weight of the inhibitor is determined by matrix assisted laser desorption ionization mass spectrometry (MALDI-MS) using a home-built instrument (Boernsen et al., Chimica (1990) 44, 412–416).

In the context of the present invention the following microorganisms have been deposited with DSM (Deutsche Sammlung von Mikroorganismen und Zellkulturen GmbH, Braunschweig, Germany) on Jun. 29, 1994:

| microorganism | accession number |
|---|---|
| pRM 3.1.10 | DSM 9268 |
| pRM 4.1.4 | DSM 9269 |
| pRM 5.1.5 | DSM 9270 |
| pRM 9.1.4 | DSM 9271 |
| pRM 11.1.4 | DSM 9272 |
| HOO5 | DSM 9273 |

LIST OF REFERENCES

1. Ako, H., Foster, R. J. & Ryan, C. A. (1972) *Biochem. Biophys. Res. Comm.* 47, 1402–7.
2. Alter, S. C., Kramps, J. A., Janoff, A. & Schwartz, L. B. (1990) *Arch. Biochem. Biophys.* 276, 26–31.
3. Atkins, P. C., Schwartz, L. B., Adkinson, N. F., von-Allmen, C., Valenzano, M. & Zweiman, B. (1990) *J. Allergy Clin. Immunol.* 86, 360–70.
4. Bieth, J. G. (1980) *Bull. europ. Physiopath. resp.* 16, 183–95.
5. Bosso, J. V., Schwartz, L. B. & Stevenson, D. D. (1991) *J. Allergy Clin. Immunol.* 88, 830–7.
6. Boukamp, P., Petrussevska, R. T., Breitkreutz, D., Hornung, J., Markham, A. & Fusenig, N. E. (1988) *J. Cell Biol.* 106, 761–71.
7. Bousquet, J., Chanez, P., Lacoste, J. Y., Enander, I., Venge, P., Peterson, C., Ahlstedt, S., Michel, F. B. & Godard, P. (1991) *J. Allergy Clin. Immunol.* 88, 649–60.
8. Broide, D. H., Gleich, G. J., Cuomo, A. J., Coburn, D. A., Federman, E. C., Schwartz, L. B. & Wasserman, S. I. (1991) *J. Allergy Clin. Immunol.* 88, 637–48.
9. Butrus, S. I., Ochsner, K. I., Abelson, M. B. & Schwartz, L. B. (1990) *Ophthalmology* 97, 1678–83.
10. Butterfield, J. H., Weiler, D. A., Hunt, L. W., Wynn, S. R. & Roche, P. C. (1990) *J. Leukocyte. Biol.* 47, 409–19.
11. Castells, M. C., Irani, A. M. & Schwartz, L. B. (1987) *J. Immunol.* 138, 2184–9.
12. Castells, M. & Schwartz, L. B. (1988) *J. Allergy Clin. Immunol.* 82, 348–55.
13. Caughey, G. H., Lazarus, S. C., Viro, N. F., Gold, W. M. & Nadel, J. A. (1988) *Immunology* 63, 339–44.
13a. Caughey, G. H., Raymond, W. W., Bacci, E., Lombardy, R. J. & Tidwell, R. R. (1993) *J. Pharmacol. Exp. Ther.* 264, 676–82.
14. Chase, T. & Shaw, E. (1970) in *Methods Enzymol Vol. XIX* (Perlmann, G. E., Lorand, & L, ed.) pp. 20–27.
15. Chung, C. H., Ives, H. E., Almeda, S. & Goldberg, A. L. (1983) *J. Biol. Chem.* 258, 11032–8.
16. Cox, S. W. & Eley, B. M. (1989) *J. Period. Res.* 24, 41–4.
17. Cromlish, J. A., Seidah, N. G., Marcinkiewicz, M., Hamelin, J., Johnson, D. A. & Chretien, M. (1987) *J. Biol. Chem.* 262, 1363–73.
18. Eley, B. M. & Cox, S. W. (1992) *J. Dent.* 20, 90–9.
19. Fink, E., Rehm, H., Gippner, C., Bode, W., Eulitz, M., Machleidt, W. & Fritz, H. (1986) *Biol. Chem. Hoppe Seyler* 367, 1235–42.
20. Franconi, G. M., Graf, P. D., Lazarus, S. C., Nadel, J. A. & Caughey, G. H. (1989) *J. Pharmacol. Exp. Ther.* 248, 947–51.
21. Friedman, M., Krull, L. H. & Cairns, J. F. (1970) *J. Biol. Chem.* 245, 3868.
22. Goldstein, S. M., Leong, J., Schwartz, L. B. & Cooke, D. (1992) *J. Immunol.* 148, 2475–82.
23. Gruber, B. L., Marchese, M. J., Suzuki, K., Schwartz, L. B., Okada, Y., Nagase, H. & Ramamurthy, N. S. (1989) *J. Clin. Invest.* 84, 1657–62.
24. Gruber, B. L. & Schwartz, L. B. (1990) *Biochem. Biophys. Res. Commun.* 171, 1272–8.
25. Hartmann, T., Ruoss, S. J., Raymond, W. W., Seuwen, K. & Caughey, G. H. (1992) *Am. J. Physiol.* 262, L528–34.
26. Harvima, I. T., Naukkarinen, A., Harvima, R. J. & Horsmanheimo, M. (1989) *Arch. Dermatol. Res.* 281, 387–91.
27. Harvima, I. T., Schechter, N. M., Harvima, R. J. & Fraki, J. E. (1988) *Biochim. Biophys. Acta* 957, 71–80.
28. Heukeshoven, J. & Dernick, R. (1985) *Electrophoresis* 6, 103–12.
29. Higgins, D. G. & Sharp, P. M. (1988) *Gene* 73, 237–44.
30. Juliusson, S., Holmberg, K., Baumgarten, C. R., Olsson, M., Enander, I. & Pipkorn, U. (1991) *Allergy* 46, 459–65.
31. Laemmli, U. K. (1970) *Nature* 227, 680–5.
32. Lipman, D. J. & Pearson, W. R. (1985) *Science* 227, 1435.
33. Maier, M., Spragg, J. & Schwartz, L. B. (1983) *J. Immunol.* 130, 2352–6.
34. Morrison, J. F. (1969) *Biochim. Biophys. Acta* 185, 269–86.
35. Ruoss, S. J., Hartmann, T. & Caughey, G. H. (1991) *J. Clin. Invest.* 88, 493–9.
36. Schwartz, L. B., Bradford, T. R., Littman, B. H. & Wintroub, B. U. (1985) *J. Immunol.* 135, 2762–7.
37. Schwartz, L. B. & Bradford, T. R. (1986) *J. Biol. Chem.* 261, 7372–9.
38. Schwartz, L. B., Lewis, R. A. & Austen, K. F. (1981) *J. Biol. Chem.* 256, 11939–43.
39. Schwartz, L. B., Lewis, R. A., Seldin, D. & Austen, K. F. (1981) *J. Immunol.* 126, 1290–4.
40. Schwartz, L. B., Metcalfe, D. D., Miller, J. S., Earl, H. & Sullivan, T. (1987) *N. Engl. J. Med.* 316, 1622–6.
41. Schwartz, L. B., Yunginger, J. W., Miller, J., Bokhari, R. & Dull, D. (1989) *J. Clin. Invest.* 83, 1551–5.
42. Sekizawa, K., Caughey, G. H., Lazarus, S. C., Gold, W. M. & Nadel, J. A. (1989) *J. Clin. Invest.* 83, 175–9.
43. Shalit, M., Schwartz, L. B., von-Allmen, C., Atkins, P. C., Lavker, R. M. & Zweiman, B. (1990) *J. Allergy Clin. Immunol.* 86, 117–25.
44. Sinha, S., Dovey, H. F., Seubert, P., Ward, P. J., Blacher, R. W., Blaber, M., Bradshaw, R. A., Arici, M., Mobley, W. C. & Lieberburg, I. (1990) *J. Biol. Chem.* 265, 8983–5.
45. Smith, T. J., Hougland, M. W. & Johnson, D. A. (1984) *J. Biol. Chem.* 259, 11046–51.
46. Smith, P. K., Krohn, R. I., Hermanson, G. T., Mallia, A. K., Gartner, F. H., Provenzano, M. D., Fujimoto, E. K., Goeke, B. J., Olson, B. J. & Klenk, D. C. (1985) *Anal. Biochem.* 150, 76.
47. Stürzebecher, J., Prasa, D. & Sommerhoff, C. P. (1992) *Biol. Chem. Hoppe-Seyler.* 373, 1025–30.
48. Tam, E. K. & Caughey, G. H. (1990) *Amer. J. Respir. Cell. Molec. Biol.* 3, 27–32.
49. Tam, E. K., Franconi, G. M., Nadel, J. A. & Caughey, G. H. (1990) *Amer. J. Respir. Cell. Molec. Biol.* 2, 449–52.
50. Walls, A. F., Bennett, A. R., Godfrey, R. C., Holgate, S. T. & Church, M. K. (1991) *Clin. Sci.* 81, 183–8.
51. Wenzel, S. E., Fowler, A. A. 3d. & Schwartz, L. B. (1988) *Am. Rev. Respir. Dis.* 137, 1002–8.
52. Chen, X.-M., Qian, Y.-W., Chi, C.-W., Gan, K. D., Zhangh, M.-F. & Chen, C.-Q. (1992) *J. Biochem.* 112, 45–51
53. Vernet, T., Dignard, D. & Thomas D. Y. (1987) *Gene* 52, 225–233

54. Sambrook, J., Fritsch, E. F. & Maniatis, T. (1989) in *Molecular cloning*: a laboratory manual, 2nd edn, Cold Spring Harbor Laboratory, Cold Spring Harbor, N.Y.
55. Skerra, A., Pfitzinger, I. & Plückthun, A. (1991) *Bio/Technology* 9, 273–278
56. Auerswald, E. A., Schröder, W. & Kotick, M. (1987) *Biol. Chem. Hoppe-Seyler* 368, 1413–1425
57. Becker, D. M. & Guarante, L. (1991) *Meth. Enzymol.* 194, 182–187
58. Devereux, J., Haeberli, P. and Smithies, O. (1984) *Nucleic Acids Res.* 12, 387–395
59. Bennetzen, J. L. & Hall, B. D. (1982) J. B. C. 257, 3026–3031 yeast and *E.coli* codon usage
60. Rose M. D., Winston, F., Hieter, P. (1990) Methods in yeast genetics; A laboratory course manual; Cold Spring Harbor Laboratory Press
61. Auerswald, E. A., Genenger, G., Mentele, R., Lenzen, S., Assfalg-Machleidt, I., Mitschang, L., Oschkinat, H. & Fritz, H. (1991) *Eur. J. Biochem.* 200, 132–138
62. Mach, H., Middaugh, C. R. & Lewis, R. V. (1992) *Anal. Biochem.* 200, 74–80
63. Achstetter et al., *Yeast* (1985), 1, 139–157
64. Hinnen et al. *Proc. Natl. Acad. Sci. USA* (1978), 75, 1929
65. Boernsen et al., *Chimica* (1990) 44, 412–416

---

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 42 amino acids
      (B) TYPE: amino acid
      (D) TOPOLOGY: linear (ii) MOLECULE TYPE: protein (iii) HYPOTHETICAL: NO (vi) ORIGINAL SOURCE:
      (A) ORGANISM: Hirudo medicinalis (xi) SEQUENCE DESCRIPTION: SEQ ID NO: 1:

```
Lys Lys Val Cys Ala Cys Pro Lys Ile Leu Lys Pro Val Cys Gly Ser
1               5                   10                  15

Asp Gly Arg Thr Tyr Ala Asn Ser Cys Ile Ala Arg Cys Asn Gly Val
            20                  25                  30

Ser Ile Lys Ser Glu Gly Ser Cys Pro Thr
            35                  40
```

(2) INFORMATION FOR SEQ ID NO: 2:

(i) SEQUENCE CHARACTERISTICS:
      (A) LENGTH: 43 amino acids
      (B) TYPE: amino acid
      (D) TOPOLOGY: linear (ii) MOLECULE TYPE: protein (iii) HYPOTHETICAL: NO (vi) ORIGINAL SOURCE:
      (A) ORGANISM: Hirudo medicinalis (xi) SEQUENCE DESCRIPTION: SEQ ID NO: 2:

```
Lys Lys Val Cys Ala Cys Pro Lys Ile Leu Lys Pro Val Cys Gly Ser
1               5                   10                  15

Asp Gly Arg Thr Tyr Ala Asn Ser Cys Ile Ala Arg Cys Asn Gly Val
            20                  25                  30

Ser Ile Lys Ser Glu Gly Ser Cys Pro Thr Gly
            35                  40
```

(2) INFORMATION FOR SEQ ID NO: 3:

(i) SEQUENCE CHARACTERISTICS:

(A) LENGTH: 46 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO: 3:

Lys Lys Val Cys Ala Cys Pro Lys Ile Leu Lys Pro Val Cys Gly Ser
    1               5                   10                  15

Asp Gly Arg Thr Tyr Ala Asn Ser Cys Ile Ala Arg Cys Asn Gly Val
                20                  25                  30

Ser Ile Lys Ser Glu Gly Ser Cys Pro Thr Gly Ile Leu Asn
            35                  40                  45

(2) INFORMATION FOR SEQ ID NO: 4:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iii) ANTI-SENSE: NO (vi) ORIGINAL SOURCE:
        (A) ORGANISM: Hirudo medicinalis (xi) SEQUENCE DESCRIPTION: SEQ ID NO: 4:

AARAARGTNT GYGCNTGYCC NAARATHYTN AARCCNGTNT GYGGNWSNGA YGGNMGNACN         60

TAYGCNAAYW SNTGYATHGC NMGNTGYAAY GGNGTNWSNA THAARWSNGA RGGNWSNTGY        120

CCNACN                                                                  126

(2) INFORMATION FOR SEQ ID NO: 5:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iii) ANTI-SENSE: NO (vi) ORIGINAL SOURCE:
        (A) ORGANISM: Hirudo medicinalis (xi) SEQUENCE DESCRIPTION: SEQ ID NO: 5:

AARAARGTNT GYGCNTGYCC NAARATHYTN AARCCNGTNT GYGGNWSNGA YGGNMGNACN         60

TAYGCNAAYW SNTGYATHGC NMGNTGYAAY GGNGTNWSNA THAARWSNGA RGGNWSNTGY        120

CCNACNGGN                                                               129

(2) INFORMATION FOR SEQ ID NO: 6:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iii) ANTI-SENSE: NO (vi) ORIGINAL SOURCE:
             (A) ORGANISM: Hirudo medicinalis (xi) SEQUENCE DESCRIPTION: SEQ ID NO: 6:

AARAARGTNT GYGCNTGYCC NAARATHYTN AARCCNGTNT GYGGNWSNGA YGGNMGNACN      60

TAYGCNAAYW SNTGYATHGC NMGNTGYAAY GGNGTNWSNA THAARWSNGA RGGNWSNTGY     120

CCNACNGGNA THYTNAAY                                                  138

(2) INFORMATION FOR SEQ ID NO: 7:

(i) SEQUENCE CHARACTERISTICS:
             (A) LENGTH: 149 base pairs
             (B) TYPE: nucleic acid
             (C) STRANDEDNESS: single
             (D) TOPOLOGY: linear (ii) MOLECULE TYPE: cDNA (iii) HYPOTHETICAL: YES (iii) ANTI-SENSE: NO (vi) ORIGINAL SOURCE:
             (A) ORGANISM: Hirudo medicinalis (xi) SEQUENCE DESCRIPTION: SEQ ID NO: 7:

ATTTCGAAGA AGGTTTGCGC ATGCCCAAAG ATCTTGAAGC CAGTCTGTGG TTCTGACGGT      60

CGTACATATG CTAACTCATG CATCGCTCGT TGTAACGGTG TATCGATCAA GTCTGAAGGT    120

TCTTGTCCAA CCGGTATTTT AAACTAATA                                      149

(2) INFORMATION FOR SEQ ID NO: 8:

(i) SEQUENCE CHARACTERISTICS:
             (A) LENGTH: 149 base pairs
             (B) TYPE: nucleic acid
             (C) STRANDEDNESS: single
             (D) TOPOLOGY: linear (ii) MOLECULE TYPE: cDNA (iii) HYPOTHETICAL: YES (iii) ANTI-SENSE: YES (vi) ORIGINAL SOURCE:
             (A) ORGANISM: Hirudo medicinalis (xi) SEQUENCE DESCRIPTION: SEQ ID NO: 8:

AGCTTATTAG TTTAAGTTAC CGGTTGGACA AGAACCTTCA GACTTGATCG ATACACCGTT      60

ACAACGAGCG ATGCATGAGT TAGCATATGT ACGACCGTCA GAACCACAGA CTGGCTTCAA    120

GATCTTTGGG CATGCGCAAA CCTTCTTCG                                      149

(2) INFORMATION FOR SEQ ID NO: 9:

(i) SEQUENCE CHARACTERISTICS:
             (A) LENGTH: 929 base pairs
             (B) TYPE: nucleic acid
             (C) STRANDEDNESS: single
             (D) TOPOLOGY: linear (ii) MOLECULE TYPE: DNA (genomic)

(ix) FEATURE:
    (A) NAME/KEY: misc_feature
    (B) LOCATION: 435..440
    (D) OTHER INFORMATION: /function= "EcoRI site"

(ix) FEATURE:
    (A) NAME/KEY: misc_feature
    (B) LOCATION: 642..647
    (D) OTHER INFORMATION: /function= "SalI site"

(ix) FEATURE:
    (A) NAME/KEY: promoter
    (B) LOCATION: 1..443
    (D) OTHER INFORMATION: /phenotype= "CUP1 promoter"

(ix) FEATURE:
    (A) NAME/KEY: sig_peptide
    (B) LOCATION: 444..500
    (D) OTHER INFORMATION: /function= "SUC2 invertase signal
        sequence"

(ix) FEATURE:
    (A) NAME/KEY: mat_peptide
    (B) LOCATION: 501..641
    (D) OTHER INFORMATION: /product= "tryptase inhibitor"

(ix) FEATURE:
    (A) NAME/KEY: terminator
    (B) LOCATION: 648..923
    (D) OTHER INFORMATION: /standard_name= "alpha-factor
        terminator"

(ix) FEATURE:
    (A) NAME/KEY: misc_feature
    (B) LOCATION: 924..929
    (D) OTHER INFORMATION: /function= "BamHI site"

(xi) SEQUENCE DESCRIPTION: SEQ ID NO: 9:

```
GATCCCCATT ACCGACATTT GGGCGCTATA CGTGCATATG TTCATGTATG TATCTGTATT      60

TAAAACACTT TTGTATTATT TTTCCTCATA TATGTGTATA GGTTTATACG GATGATTTAA     120

TTATTACTTC ACCACCCTTT ATTTCAGGCT GATATCTTAG CCTTGTTACT AGTTAGAAAA     180

AGACATTTTT GCTGTCAGTC ACTGTCAAGA GATTCTTTTG CTGGCATTTC TTCTAGAAGC     240

AAAAAGAGCG ATGCGTCTTT TCCGCTGAAC CGTTCCAGCA AAAAAGACTA CCAACGCAAT     300

ATGGATTGTC AGAATCATAT AAAAGAGAAG CAAATAACTC CTTGTCTTGT ATCAATTGCA     360

TTATAATATC TTCTTGTTAG TGCAATATCA TATAGAAGTC ATCGAAATAG ATATTAAGAA     420

AAACAAACTG TAACGAATTC AAAATGCTTT TGCAAGCTTT CCTTTTCCTT TTGGCTGGTT     480

TTGCAGCCAA AATATCTGCA AGAAGGTTT GCGCCTGTCC AAAGATTTG AAGCCAGTTT       540

GTGGTTCTGA CGGTCGTACC TACGCCAACT CTTGTATTGC CCGTTGTAAC GGTGTTTCTA     600

TTAAGTCTGA AGGTTCTTGT CCAACCGGTA TTTTGAACTG AGTCGACTTT GTTCCCACTG     660

TACTTTTAGC TCGTACAAAA TACAATATAC TTTTCATTTC TCCGTAAACA ACATGTTTTC     720

CCATGTAATA TCCTTTTCTA TTTTTCGTTC CGTTACCAAC TTTACACATA CTTTATATAG     780

CTATTCACTT CTATACACTA AAAAACTAAG ACAATTTTAA TTTTGCTGCC TGCCATATTT     840

CAATTTGTTA TAAATTCCTA TAATTTATCC TATTAGTAGC TAAAAAAAGA TGAATGTGAA     900

TCGAATCCTA AGAGAATTAA TTCGGATCC                                       929
```

(2) INFORMATION FOR SEQ ID NO: 10:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 10:

GTGCGAATTC AAAATGAGAT TTCCTTCAAT TTTTACTGCA G                41

(2) INFORMATION FOR SEQ ID NO: 11:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:11:

CAAAGTCGAC TTTATCCAGC AAGATCTCTT CTTCTTTAGC AGCAATGC         48

(2) INFORMATION FOR SEQ ID NO: 12:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO: 12:

GAAGAGATCT TGCTGGATAA AGTCGACTTT GTTCCCACTG TACTTTTAGC       50

(2) INFORMATION FOR SEQ ID NO: 13:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO: 13:

CCGGGGATCC GAATTAATTCT CTTAGGATT CG                          32

(2) INFORMATION FOR SEQ ID NO: 14:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO: 14:

TAGAGGATCC CCATTACCGA CATTTGGGCG CTATACGTGC                  40

(2) INFORMATION FOR SEQ ID NO: 15:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO: 15:

CGACGAATTC ACAGTTTGTT TTTCTTAATA TCTATTTCG                   39

(2) INFORMATION FOR SEQ ID NO: 16:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 16:

```
AAAGATCTTG CTGGATAAAA GAAAGAAGGT TTGCGCCTGT CCAAAGATTT TGAAGCCAGT    60

TTGTGGTTCT GACGGTCGTA CC                                            82
```

(2) INFORMATION FOR SEQ ID NO: 17:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 17:

```
ACAAGAACTT CAGACTTAAT AGAAACACCG TTACAACGGG CAATACAAGA GTTGGCGTAG    60

GTACGACCGT CAGAACCAC                                                79
```

(2) INFORMATION FOR SEQ ID NO: 18:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 18:

```
TTGTCGACTC AGTTCAAAAT ACCGGTTGGA CAAGAACCTT CAGACTTAA                49
```

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 19:

```
TTGTCGACTC AGTTCAAAAT A                                             21
```

(2) INFORMATION FOR SEQ ID NO: 20:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 20:

```
AAGAATTCAT GCTTTTGCAA GCTTTCCTTT TCCTTTTGGC TGGTTTTGCA GCCAAAATAT    60
```

```
CTGCAAAGAA GGTTTGCGCC TGTC                                                    84
```

(2) INFORMATION FOR SEQ ID NO: 21:

(i) SEQUENCE CHARACTERISTICS:
        (A) LENGTH: 22 amino acids
        (B) TYPE: amino acid
        (D) TOPOLOGY: linear (ii) MOLECULE TYPE: protein (iii) HYPOTHETICAL: YES (xi) SEQUENCE DESCRIPTION: SEQ ID NO: 21:

```
Cys Pro Lys Ile Leu Lys Pro Val Xaa Gly Ser Asp Gly Arg Thr
 1               5                  10                  15

Tyr Ala Asn Ser Cys Ile Ala
            20
```

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iii) ANTI-SENSE: NO (vi) ORIGINAL SOURCE:
        (A) ORGANISM: Hirudo medicinalis (xi) SEQUENCE DESCRIPTION: SEQ ID NO: 22:

```
CTAGATAAAA GAAAGAAGGT TTGCGCATGV                                               30
```

(2) INFORMATION FOR SEQ ID NO: 23:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iii) ANTI-SENSE: NO (vi) ORIGINAL SOURCE:
        (A) ORGANISM: Hirudo medicinalis (xi) SEQUENCE DESCRIPTION: SEQ ID NO: 23:

```
AATTCGGATC C                                                                  11
```

(2) INFORMATION FOR SEQ ID NO: 24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iii) ANTI-SENSE: NO (vi) ORIGINAL SOURCE:
    (A) ORGANISM: Hirudo medicinalis (xi) SEQUENCE DESCRIPTION: SEQ ID NO: 24:

CGCAGTAGCG GTAAACG                17

We claim:

1. An isolated and purified polypeptide tryptase inhibitor comprising the amino acid sequence:
Lys-Lys-Val-Cys-Ala-Cys-Pro-Lys-lle-Leu 10
Lys-Pro-Val-Cys-Gly-Ser-Asp-Gly-Arg-Thr 20
Tyr-Ala-Asn-Ser-Cys-lle-Ala-Arg-Cys-Asn 30
Gly-Val-Ser-lle-Lys-Ser-Glu-Gly-Ser-Cys 40
Pro-Thr-X 42
wherein the c-terminal residue X represents H (SEQ ID NO:1) -Gly (SEQ ID NO:2) or -Gly-lle-Leu-Asn (SEQ ID NO:3).

2. An isolated and purified polypeptide tryptase inhibitor comprising the amino acid sequence SEQ ID NO: 21
$R^1$-Cys-Pro-Lys-lle-Leu
Lys-Pro-Val-Z-Gly-Ser-Asp-Gly-Arg-Thr
Tyr-Ala-Asn-Ser-Cys-lle-Ala-$R^2$
wherein
the N-terminal residue $R^1$ represents Ala- or Cys-Ala-;
the C-terminal residue $R^2$ represents -Arg or -Arg-Cys; and
Z defines any amino acid.

3. A pharmaceutical composition comprising a tryptase inhibiting amount of a polypeptide according to claims 1 and 2 optionally in combination with a pharmaceutically acceptable carrier of diluent.

4. The expression cassette comprising a promoter operably linked to a first DNA sequence encoding a signal peptide linked in the proper reading frame to a second polypeptide encoding DNA sequence of SEQ ID NO:9 and a DNA sequence containing transcription termination signals.

5. The expression cassette according to claim 4 wherein the promoter is selected from the group consisting of CUP1 p, and GAPDHp.

6. The expression cassette according to claim 4 wherein the signal sequence is selected from the group consisting of the α-factor leader, PHO5, and SUC2.

7. The expression cassette according to claim 4 wherein the terminator is selected from the group consisting of the α-factor terminator and PHO5 terminator.

8. A vector for the transformation of eukaryotic or prokaryotic hosts comprising an expression cassette as defined in claim 4.

9. The vector of claim 8 which is a two-micron based yeast vector.

10. The vector of claim 8 selected from
a) pRM9.1.4 as deposited with the DSM and having the accession number DSM 9271;
b) pRM11.1.4 as deposited with the DSM and having the accession number DSM 9272;
c) pRM5.1.5 as deposited with the DSM and having the accession number DSM 9270;
d) pRM4.1.4 as deposited with the DSM and having the accession number DSM 9269; and
e) pRM3.1.10 as deposited with the DSM and having the accession number DSM 9268.

* * * * *